(12) United States Patent
Parramon et al.

(10) Patent No.: US 11,590,350 B2
(45) Date of Patent: Feb. 28, 2023

(54) SYSTEMS AND METHODS FOR DELIVERING SPINAL CORD STIMULATION THERAPY

(71) Applicant: Boston Scientific Neuromodulation Corporation, Valencia, CA (US)

(72) Inventors: Jordi Parramon, Valencia, CA (US); Que T. Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 61 days.

(21) Appl. No.: 16/989,176

(22) Filed: Aug. 10, 2020

(65) Prior Publication Data

US 2020/0368529 A1 Nov. 26, 2020

Related U.S. Application Data

(63) Continuation of application No. 15/681,765, filed on Aug. 21, 2017, now Pat. No. 10,780,274.
(Continued)

(51) Int. Cl.
*A61N 1/36* (2006.01)
*A61N 1/05* (2006.01)
*A61N 1/372* (2006.01)

(52) U.S. Cl.
CPC ....... *A61N 1/36062* (2017.08); *A61N 1/0551* (2013.01); *A61N 1/36071* (2013.01); *A61N 1/36171* (2013.01); *A61N 1/372* (2013.01)

(58) Field of Classification Search
CPC .. A61N 1/0551; A61N 1/0553; A61N 1/0556; A61N 1/0558; A61N 1/36021; A61N 1/3605; A61N 1/36053; A61N 1/36057; A61N 1/3606; A61N 1/36062; A61N 1/36071; A61N 1/36075;
(Continued)

(56) References Cited

U.S. PATENT DOCUMENTS 5,948,007 A 9/1999 Starkebaum et al.
6,094,598 A 7/2000 Elsberry et al.
(Continued)

FOREIGN PATENT DOCUMENTS

AU 2014233252 B2 7/2017
AU 2017204544 B2 1/2019
(Continued)

OTHER PUBLICATIONS

"U.S. Appl. No. 14/199,845, Advisory Action dated Dec. 24, 2015", 3 pgs.
(Continued)

*Primary Examiner* — Brian T Gedeon
(74) *Attorney, Agent, or Firm* — Schwegman Lundberg & Woessner, P.A.

(57) ABSTRACT

This document discusses, among other things, systems and methods to provide a paresthesia therapy to a patient using an implantable neuromodulation system, wherein providing the paresthesia therapy may include delivering to the patient an electrical waveform having a duration and a distribution of frequencies in the range of 0.001 kHz to 20 kHz, wherein the distribution of frequencies includes a first frequency group of one or more frequencies and a second frequency group of one or more frequencies, and wherein the patient continuously experiences paresthesia throughout the duration of the electrical waveform.

20 Claims, 8 Drawing Sheets

Related U.S. Application Data

(60) Provisional application No. 62/378,007, filed on Aug. 22, 2016.

(58) Field of Classification Search
CPC ............ A61N 1/36167; A61N 1/36189; A61N 1/36192; A61N 1/36196; A61N 1/39624
See application file for complete search history.

(56) References Cited

U.S. PATENT DOCUMENTS

| | | |
|---|---|---|
| 6,181,969 B1 | 1/2001 | Gord |
| 6,337,997 B1 | 1/2002 | Rise |
| 6,516,227 B1 | 2/2003 | Meadows et al. |
| 6,609,029 B1 | 8/2003 | Mann et al. |
| 6,609,032 B1 | 8/2003 | Woods et al. |
| 6,675,046 B2 | 1/2004 | Holsheimer |
| 6,741,892 B1 | 5/2004 | Meadows et al. |
| 6,895,280 B2 | 5/2005 | Meadows et al. |
| 6,993,384 B2 | 1/2006 | Bradley et al. |
| 7,244,150 B1 | 7/2007 | Brase et al. |
| 7,317,948 B1 | 1/2008 | King et al. |
| 7,321,797 B2 | 1/2008 | Blamey et al. |
| 7,333,857 B2 | 2/2008 | Campbell |
| 7,359,751 B1 | 4/2008 | Erickson et al. |
| 7,539,538 B2 | 5/2009 | Parramon et al. |
| 7,650,184 B2 | 1/2010 | Walter |
| 7,672,734 B2 | 3/2010 | Anderson et al. |
| 7,761,165 B1 | 7/2010 | He et al. |
| 7,761,166 B2 | 7/2010 | Gerber et al. |
| 7,783,353 B2 | 8/2010 | Libbus et al. |
| 7,949,395 B2 | 5/2011 | Kuzma |
| 7,974,698 B2 | 7/2011 | Tass et al. |
| 7,974,706 B2 | 7/2011 | Moffitt et al. |
| 7,979,133 B2 | 7/2011 | Feler et al. |
| 8,019,439 B2 | 9/2011 | Kuzma et al. |
| 8,170,675 B2 | 5/2012 | Alataris et al. |
| 8,175,710 B2 | 5/2012 | He |
| 8,209,021 B2 | 6/2012 | Alataris et al. |
| 8,224,436 B2 | 7/2012 | Libbus et al. |
| 8,224,450 B2 | 7/2012 | Brase |
| 8,224,453 B2 | 7/2012 | De Ridder |
| 8,255,057 B2 | 8/2012 | Fang et al. |
| 8,285,389 B2 | 10/2012 | Libbus et al. |
| 8,355,792 B2 | 1/2013 | Alataris et al. |
| 8,355,797 B2 | 1/2013 | Caparso et al. |
| 8,359,102 B2 | 1/2013 | Alataris et al. |
| 8,359,103 B2 | 1/2013 | Alataris et al. |
| 8,364,278 B2 | 1/2013 | Pianca et al. |
| 8,380,318 B2 | 2/2013 | Kishawi et al. |
| 8,396,559 B2 | 3/2013 | Alataris et al. |
| 8,401,640 B2 | 3/2013 | Zhao et al. |
| 8,406,876 B2 | 3/2013 | McCabe et al. |
| 8,412,345 B2 | 4/2013 | Moffitt |
| 8,423,147 B2 | 4/2013 | Alataris et al. |
| 8,455,716 B2 | 6/2013 | Huang et al. |
| 8,473,061 B2 | 6/2013 | Moffitt et al. |
| 8,504,147 B2 | 8/2013 | Deem et al. |
| 8,527,042 B2 | 9/2013 | Libbus et al. |
| 8,571,665 B2 | 10/2013 | Moffitt et al. |
| 8,615,300 B2 | 12/2013 | Feler et al. |
| 8,649,874 B2 | 2/2014 | Alataris et al. |
| 8,660,653 B2 | 2/2014 | Kothandaraman |
| 8,670,831 B2 | 3/2014 | Wacnik et al. |
| 8,676,329 B2 | 3/2014 | Wacnik et al. |
| 8,676,331 B2 | 3/2014 | Parker |
| 8,700,178 B2 | 4/2014 | Anderson |
| 8,731,675 B2 | 5/2014 | Ranu et al. |
| 8,751,009 B2 | 6/2014 | Wacnik |
| 8,792,993 B2 | 7/2014 | Pianca et al. |
| 8,874,211 B2 | 10/2014 | Libbus et al. |
| 8,880,170 B2 | 11/2014 | Bradley et al. |
| 8,909,350 B2 | 12/2014 | Lee |
| 8,923,981 B2 | 12/2014 | Grill, Jr. et al. |
| 9,002,459 B2 | 4/2015 | Lee et al. |
| 9,095,712 B2 | 8/2015 | Lee |
| 9,186,522 B2 | 11/2015 | Ternes |
| 9,220,900 B2 | 12/2015 | Libbus et al. |
| 9,265,948 B2 | 2/2016 | Libbus et al. |
| 9,630,012 B2 | 4/2017 | Carroll |
| 9,694,183 B2 | 7/2017 | Grandhe et al. |
| 9,744,365 B2 | 8/2017 | Davis et al. |
| 9,950,173 B2 | 4/2018 | Doan |
| 9,993,646 B2 | 6/2018 | Parramon et al. |
| 10,029,102 B2 | 7/2018 | Doan et al. |
| 10,039,930 B2 | 8/2018 | Vallejo et al. |
| 10,226,626 B2 | 3/2019 | Alataris et al. |
| 10,780,274 B2 | 9/2020 | Parramon et al. |
| 11,040,206 B2 | 6/2021 | Doan |
| 11,311,726 B2 | 4/2022 | Vansickle et al. |
| 2003/0120323 A1 | 6/2003 | Meadows et al. |
| 2003/0139781 A1 | 7/2003 | Bradley et al. |
| 2004/0215286 A1 | 10/2004 | Stypulkowski |
| 2005/0267546 A1 | 12/2005 | Parramon et al. |
| 2006/0200205 A1 | 9/2006 | Haller |
| 2006/0212089 A1 | 9/2006 | Tass |
| 2006/0259099 A1 | 11/2006 | Goetz et al. |
| 2007/0100377 A1 | 5/2007 | Armstrong et al. |
| 2007/0150036 A1 | 6/2007 | Anderson |
| 2007/0168004 A1 | 7/2007 | Walter |
| 2007/0168007 A1 | 7/2007 | Kuzma et al. |
| 2007/0203521 A1 | 8/2007 | Dobak et al. |
| 2008/0021504 A1 | 1/2008 | McCabe et al. |
| 2008/0188909 A1 | 8/2008 | Bradley |
| 2008/0294211 A1 | 11/2008 | Moffitt |
| 2009/0131995 A1 | 5/2009 | Sloan et al. |
| 2009/0204173 A1 | 8/2009 | Fang et al. |
| 2009/0281596 A1 | 11/2009 | King et al. |
| 2010/0010566 A1 | 1/2010 | Thacker et al. |
| 2010/0023070 A1 | 1/2010 | Moffitt et al. |
| 2010/0057162 A1 | 3/2010 | Moffitt et al. |
| 2010/0121408 A1 | 5/2010 | Imran et al. |
| 2010/0121409 A1 | 5/2010 | Kothandaraman et al. |
| 2010/0191307 A1 | 7/2010 | Fang et al. |
| 2010/0198300 A1 | 8/2010 | Smith |
| 2010/0249875 A1 | 9/2010 | Kishawi et al. |
| 2010/0268298 A1 | 10/2010 | Moffitt et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2010/0280440 A1 | 11/2010 | Skelton et al. |
| 2011/0005069 A1 | 1/2011 | Pianca |
| 2011/0009923 A1 | 1/2011 | Lee |
| 2011/0054568 A1 | 3/2011 | Lane et al. |
| 2011/0071593 A1 | 3/2011 | Parker et al. |
| 2011/0078900 A1 | 4/2011 | Pianca et al. |
| 2011/0106215 A1 | 5/2011 | Moffitt |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0137370 A1 | 6/2011 | Gross et al. |
| 2011/0238129 A1 | 9/2011 | Moffitt |
| 2011/0251583 A1 | 10/2011 | Miyazawa et al. |
| 2011/0264156 A1 | 10/2011 | Mukherjee et al. |
| 2012/0016378 A1 | 1/2012 | Pianca et al. |
| 2012/0016448 A1 | 1/2012 | Lee |
| 2012/0041511 A1 | 2/2012 | Lee |
| 2012/0041518 A1 | 2/2012 | Kim et al. |
| 2012/0046710 A1 | 2/2012 | DiGiore et al. |
| 2012/0059446 A1 | 3/2012 | Wallace et al. |
| 2012/0071949 A1 | 3/2012 | Pianca et al. |
| 2012/0083709 A1 | 4/2012 | Parker et al. |
| 2012/0089200 A1 | 4/2012 | Ranu et al. |
| 2012/0095524 A1 | 4/2012 | Nelson et al. |
| 2012/0165911 A1 | 6/2012 | Pianca |
| 2012/0197336 A1 | 8/2012 | Su |
| 2012/0197375 A1 | 8/2012 | Pianca et al. |
| 2012/0203304 A1 | 8/2012 | Alataris et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |

(56) References Cited

U.S. PATENT DOCUMENTS

| | | |
|---|---|---|
| 2012/0239109 A1 | 9/2012 | Lee |
| 2012/0253422 A1 | 10/2012 | Thacker et al. |
| 2012/0265279 A1 | 10/2012 | Zhu et al. |
| 2012/0283797 A1 | 11/2012 | De Ridder |
| 2012/0290041 A1 | 11/2012 | Kim et al. |
| 2013/0041425 A1 | 2/2013 | Fang et al. |
| 2013/0066331 A1 | 3/2013 | Chitre et al. |
| 2013/0066411 A1 | 3/2013 | Thacker et al. |
| 2013/0073007 A1 | 3/2013 | Parker et al. |
| 2013/0116752 A1 | 5/2013 | Parker et al. |
| 2013/0131760 A1 | 5/2013 | Rao et al. |
| 2013/0158628 A1 | 6/2013 | Kothandaraman |
| 2013/0158630 A1 | 6/2013 | Lee |
| 2013/0197424 A1 | 8/2013 | Bedenbaugh |
| 2013/0197602 A1 | 8/2013 | Pianca et al. |
| 2013/0218232 A1 | 8/2013 | Giftakis et al. |
| 2013/0268021 A1 | 10/2013 | Moffitt |
| 2013/0282078 A1 | 10/2013 | Wacnik |
| 2013/0289647 A1 | 10/2013 | Bhadra et al. |
| 2013/0296975 A1 | 11/2013 | Lee et al. |
| 2014/0039587 A1 | 2/2014 | Romero |
| 2014/0081349 A1 | 3/2014 | Lee et al. |
| 2014/0163627 A1 | 6/2014 | Starr et al. |
| 2014/0163660 A1 | 6/2014 | Fang et al. |
| 2014/0243926 A1 | 8/2014 | Carcieri |
| 2014/0249599 A1 | 9/2014 | Kaula et al. |
| 2014/0277267 A1 | 9/2014 | Vansickle et al. |
| 2014/0277281 A1 | 9/2014 | Grandhe |
| 2014/0343622 A1 | 11/2014 | Alataris et al. |
| 2014/0035821 A1 | 12/2014 | Howard |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0364919 A1 | 12/2014 | Doan |
| 2014/0379043 A1 | 12/2014 | Howard |
| 2015/0018898 A1 | 1/2015 | Tass |
| 2015/0018915 A1 | 1/2015 | Leven |
| 2015/0032181 A1 | 1/2015 | Baynham et al. |
| 2015/0045864 A1 | 2/2015 | Howard |
| 2015/0051681 A1 | 2/2015 | Hershey |
| 2015/0066120 A1 | 3/2015 | Govea |
| 2015/0134031 A1 | 5/2015 | Moffitt et al. |
| 2015/0151113 A1 | 6/2015 | Govea et al. |
| 2015/0209587 A1 | 7/2015 | Lee et al. |
| 2015/0328461 A1 | 11/2015 | Charlesworth et al. |
| 2016/0082256 A1 | 3/2016 | Moffitt et al. |
| 2016/0263380 A1 | 9/2016 | Starr et al. |
| 2017/0128729 A1 | 5/2017 | Netoff et al. |
| 2017/0281948 A1 | 10/2017 | Grandhe |
| 2018/0050204 A1 | 2/2018 | Parramon et al. |
| 2018/0193653 A1 | 7/2018 | Bokil |
| 2018/0221668 A1 | 8/2018 | Doan |
| 2018/0228421 A1 | 8/2018 | Saab |
| 2018/0289967 A1 | 10/2018 | Bokil |
| 2019/0083785 A1 | 3/2019 | Tass et al. |
| 2019/0184168 A1 | 6/2019 | Vansickle et al. |
| 2019/1841671 | 6/2019 | Vansickle et al. |
| 2022/0226655 A1 | 7/2022 | Vansickle et al. |

FOREIGN PATENT DOCUMENTS

| | | |
|---|---|---|
| AU | 2018251564 B2 | 10/2020 |
| CN | 101516436 A | 8/2009 |
| CN | 105183802 A | 12/2015 |
| CN | 105209111 A | 12/2015 |
| CN | 105163802 B | 8/2017 |
| CN | 105209111 B | 9/2017 |
| CN | 107551402 A | 1/2018 |
| CN | 110769892 A | 2/2020 |
| CN | 107551402 B | 6/2021 |
| CN | 113368397 A | 9/2021 |
| DE | 102012002437 A1 | 8/2013 |
| EP | 2207587 | 5/2009 |
| EP | 2968932 B1 | 10/2017 |
| EP | 2968933 B1 | 6/2019 |
| EP | 3583979 A1 | 12/2019 |
| EP | 3583979 B1 | 4/2021 |
| JP | 2011502586 A | 1/2011 |
| JP | 2016512758 A | 5/2016 |
| WO | WO-2005087314 A1 | 9/2005 |
| WO | WO-2006029257 A2 | 3/2006 |
| WO | WO-2006135791 A2 | 12/2006 |
| WO | WO-2009061813 A1 | 5/2009 |
| WO | WO-2009061813 A9 | 5/2009 |
| WO | WO-2010069317 A1 | 6/2010 |
| WO | WO-2014145222 A2 | 9/2014 |
| WO | WO-2014145222 A3 | 9/2014 |
| WO | WO-2014197564 A1 | 12/2014 |
| WO | WO-2017027703 A1 | 2/2017 |
| WO | WO-2018039117 A1 | 3/2018 |
| WO | WO-2018191097 A1 | 10/2018 |

OTHER PUBLICATIONS

"U.S. Appl. No. 14/199,845, Examiner Interview Summary dated Feb. 1, 2017", 3 pgs.

"U.S. Appl. No. 14/199,845, Final Office Action dated Sep. 29, 2016", 12 pgs.

"U.S. Appl. No. 14/199,845, Final Office Action dated Oct. 15, 2015", 14 pgs.

"U.S. Appl. No. 14/199,845, Non Final Office Action dated Mar. 12, 2015", 11 pgs.

"U.S. Appl. No. 14/199,845, Non Final Office Action dated Mar. 23, 2016", 12 pgs.

"U.S. Appl. No. 14/199,845, Notice of Allowance dated Mar. 3, 2017", 8 pgs.

"U.S. Appl. No. 14/199,845, Preliminary Amendment filed Mar. 6, 2014", 6 pgs.

"U.S. Appl. No. 14/199,845, Response filed Jan. 30, 2017 to Final Office Action dated Sep. 29, 2016", 9 pgs.

"U.S. Appl. No. 14/199,845, Response filed Jun. 22, 2016 to Non Final Office Action dated Mar. 23, 2016", 9 pgs.

"U.S. Appl. No. 14/199,845, Response filed Jul. 10, 2015 to Non Final Office Action dated Mar. 12, 2015", 10 pgs.

"U.S. Appl. No. 14/199,845, Response filed Dec. 15, 2015 to Final Office Action dated Oct. 15, 2015", 10 pgs.

"U.S. Appl. No. 14/214,752, Advisory Action dated Feb. 16, 2017", 10 pgs.

"U.S. Appl. No. 14/214,752, Advisory Action dated Jun. 7, 2016", 5 pgs.

"U.S. Appl. No. 14/214,752, Appeal Brief filed Apr. 27, 2017", 48 pgs.

"U.S. Appl. No. 14/214,752, Appeal Decision dated Dec. 14, 2018", 14 pgs.

"U.S. Appl. No. 14/214,752, Applicant's Summary of Examiner Interview filed Apr. 27, 2017", 1 pg.

"U.S. Appl. No. 14/214,752, Examiner Interview Summary dated Jan. 22, 2019", 3 pgs.

"U.S. Appl. No. 14/214,752, Examiner Interview Summary dated Feb. 7, 2017", 4 pgs.

"U.S. Appl. No. 14/214,752, Final Office Action dated Apr. 1, 2016", 22 pgs.

"U.S. Appl. No. 14/214,752, Final Office Action dated Dec. 5, 2016", 36 pgs.

"U.S. Appl. No. 14/214,752, Non Final Office Action dated Mar. 26, 2019", 17 pgs.

"U.S. Appl. No. 14/214,752, Non Final Office Action dated Sep. 1, 2016", 35 pgs.

"U.S. Appl. No. 14/214,752, Non Final Office Action dated Dec. 11, 2015", 16 pgs.

"U.S. Appl. No. 14/214,752, Preliminary Amendment filed Mar. 15, 2014", 43 pgs.

"U.S. Appl. No. 14/214,452, Response filed Feb. 6, 2017 to Final Office Action dated Dec. 5, 2016", 21 pgs.

"U.S. Appl. No. 14/214,752, Response filed Mar. 11, 2016 to Non Final Office Action dated Dec. 11, 2015", 12 pgs.

(56) References Cited

OTHER PUBLICATIONS

"U.S. Appl. No. 14/214,752, Response filed Jun. 1, 2016 to Final Office Action dated Apr. 1, 2016", 18 pgs.
"U.S. Appl. No. 14/214,752, Response filed Nov. 16, 2015 to Restriction Requirement dated Sep. 15, 2015", 8 pgs.
"U.S. Appl. No. 14/214,752, Restriction Requirement dated Sep. 15, 2015", 7 pgs.
"U.S. Appl. No. 14/214,752, Response filed Nov. 14, 2016 to Non Final Office Action dated Sep. 1, 2016", 19 pgs.
"U.S. Appl. No. 14/295,735, Non Final Office Action dated Mar. 29, 2017", 15 pgs.
"U.S. Appl. No. 14/295,735, Notice of Allowance dated Dec. 12, 2017", 9 pgs.
"U.S. Appl. No. 14/295,735, Response fiied Oct. 27, 2016 to Restriction Requirement dated Aug. 29, 2016", 10 pgs.
"U.S. Appl. No. 14/295,735, Restriction Requirement dated Aug. 29, 2016", 7 pgs.
"U.S. Appl. No. 14/296,735, Response filed Jun. 26, 2017 to Non Final Office Action dated Mar. 29, 2017", 10 pgs.
"U.S. Appl. No. 15/629,968, Examiner Interview Summary dated Mar. 25, 2019", 4 pgs.
"U.S. Appl. No. 15/629,968, Final Office Action dated Jul. 13, 2018", 12 pgs.
"U.S. Appl. No. 15/629,968, Non Final Office Action dated Jan. 8, 2018", 12 pgs.
"U.S. Appl. No. 15/629,968, Non Final Office Action dated Mar. 6, 2019", 11 pgs.
"U.S. Appl. No. 15/629,968, Preliminary Amendment filed Jun. 26, 2017", 7 pgs.
"U.S. Appl. No. 15/629,968, Response filed Mar. 22, 2018 to Non Final Office Action dated Jan. 8, 2018", 10 pgs.
"U.S. Appl. No. 15/629,968, Response filed Oct. 15, 2018 to Final Office Action dated Jul. 13, 2018", 11 pgs.
"U.S. Appl. No. 15/681,765, Amendment Under 37 CFR 1.114 filed Apr. 13, 2020", 6 pgs.
"U.S. Appl. No. 15/681,765, Final Office Action dated Sep. 16, 2019", 11 pgs.
"U.S. Appl. No. 15/681,765, Non Final Office Action dated Mar. 19, 2019", 11 pgs.
"U.S. Appl. No. 15/681,765, Notice of Allowance dated Jan. 13, 2020", 9 pgs.
"U.S. Appl. No. 15/681,765, Notice of Allowance dated May 5, 2020", 6 pgs.
"U.S. Appl. No. 15/681,765, Response filed Dec. 18, 2019 to Final Office Action dated Sep. 16, 2019", 8 pgs.
"U.S. Appl. No. 15/681,765, Response filed Jun. 19, 2019 to Non-Final Office Action dated Mar. 19, 2019", 8 pgs.
"U.S. Appl. No. 15/865,805, Non Final Office Action dated Oct. 22, 2019", 10 pgs.
"U.S. Appl. No. 15/865,805, Notice of Allowance dated Mar. 24, 2020", 5 pgs.
"U.S. Appl. No. 15/865,805, Response filed Jan. 23, 2020 to Non Final Office Action dated Oct. 22, 2019", 9 pgs.
"U.S. Appl. No. 15/865,805, Response filed Sep. 23, 2019 to Restriction Requirement dated Jul. 25, 2019", 8 pgs.
"U.S. Appl. No. 15/865,805, Restriction Requirement dated Jul. 25, 2019", 9 pgs.
"U.S. Appl. No. 15/945,028, Non Final Office Action dated Apr. 6, 2020", 7 pgs.
"U.S. Appl. No. 15/945,028, Response filed Feb. 4, 2020 to Restriction Requirement dated Nov. 18, 2019", 6 pgs.
"U.S. Appl. No. 15/945,028, Restriction Requirement dated Nov. 18, 2019", 7 pgs.
"U.S. Appl. No. 16/275,730, Preliminary Amendment filed Mar. 7, 2019", 11 pgs.
"U.S. Appl. No. 16/275,892, Preliminary Amendment filed Mar. 7, 2019", 9 pgs.
"Australian Application Serial No. , Response filed Mar. 2, 2017 to Examiners Report dated May 2, 2016", 25 pgs.
"Australian Application Serial No. 2014233252, Response filed Feb. 28, 2017 to First Examiners Report dated Jun. 22, 2016", 9 pgs.
"Australian Application Serial No. 2014237683, Subsequent Examiners Report dated Apr. 12, 2017", 8 pgs.
"Australian Application Serial No. 2017204544, First Examination Report dated Nov. 29, 2017", 5 pgs.
"Australian Application Serial No. 2017204544, Response filed Sep. 11, 2018 to Subsequent Examiners Report dated May 4, 2018", 64 pgs.
"Australian Application Serial No. 2017204544, Subsequent Examiners Report dated May 4, 2018", 6 pgs.
"Australian Application Serial No. 2017204544, Voluntary Amendment filed Jul. 17, 2017", 8 pgs.
"Australian Application Serial No. 2018251564, First Examination Report dated Feb. 28, 2020", 4 pgs.
"Australian Application Serial No. 2018274915, First Examination Report dated Feb. 25, 2020", 3 pgs.
"Canadian Application Serial No. 2,906,940, Office Action dated Jun. 20, 2017", 4 pgs.
"Canadian Application Serial No. 2,906,940, Office Action dated Aug. 2, 2016", 5 pgs.
"Canadian Application Serial No. 2,906,940, Response filed Feb. 2, 2017 to Office Action dated Aug. 2, 2016", 20 pgs.
"Chinese Application Serial No. 201480023976.9, Office Action dated Jun. 1, 2016", With English Translation, 18 pgs.
"Chinese Application Serial No. 201480023976.9, Office Action dated Dec. 30, 2016", With English translation, 12 pgs.
"Chinese Application Serial No. 201480023976.9, Response filed Mar. 10, 2017 to Office Action dated Dec. 30, 2016", w/ claims in English, 9 pgs.
"Chinese Application Serial No. 201480023976.9, Response filed Oct. 12, 2016 to Office Action dated Jun. 1, 2016", With English claims, 14 pgs.
"Chinese Application Serial No. 201480026970.7, Office Action dated Jan. 12, 2017", (with English translation), 11 pgs.
"Chinese Application Serial No. 201480026970.7, Office Action dated May 5, 2017", w/ brief summary from agent's letter, 4 pgs.
"Chinese Application Serial No. 201480026970.7, Office Action dated Jul. 6, 2016", With English Translation, 31 pgs.
"Chinese Application Serial No. 201480026970.7, Response filed Mar. 24, 2017 to Office Action dated Jan. 12, 2017", w/ Claims in English, 17 pgs.
"Chinese Application Serial No. 201480026970.7, Response filed Jun. 28, 2017 to Office Action dated May 5, 2017", w/ claims in English, 17 pgs.
"Chinese Application Serial No. 201480026970.7, Response filed Nov. 21, 2016 to Office Action dated Jul. 6, 2016", w/ claims in English, 134 pgs.
"European Application Serial No. 14715815.8, Communication Pursuant to Article 94(3) EPC dated May 8, 2017", 7 pgs.
"European Application Serial No. 14715815.8, Response filed Oct. 16, 2017 to Communication Pursuant to Article 94(3) EPC dated May 8, 2017", 12 pgs.
"European Application Serial No. 18712707.1, Response to Communication Pursuant to Rules 161 and 162 filed Mar. 17, 2020", 13 pgs.
"European Application Serial No. 19179413.0, Extended European Search Report dated Nov. 8, 2019", 7 pgs.
"International Application Serial No. PCT/US2018/026186, International Preliminary Report on Patentability dated Oct. 24, 2019", 8 pgs.
"International Application Serial No. PCT/US2014/021397, International Preliminary Report on Patentability dated Sep. 24, 2015", 9 pgs.
"International Application Serial No. PCT/US2014/021397, International Search Report dated Jun. 10, 2014", 4 pgs.
"International Application Serial No. PCT/US2014/029945, International Preliminary Report on Patentability dated Sep. 24, 2015", 9 pgs.
"International Application Serial No. PCT/US2014/029945, International Search Report dated Nov. 13, 2014", 8 pgs.

(56) References Cited

OTHER PUBLICATIONS

"International Application Serial No. PCT/US2014/029945, Invitation to Pay Additional Fees and Partial Search Report dated Jun. 11, 2014", 5 pgs.
"International Application Serial No. PCT/US2014/029945, Written Opinion dated Nov. 13, 2014", 7 pgs.
"International Application Serial No. PCT/US2014/40860, International Preliminary Report on Patentability dated Dec. 17, 2015", 8 pgs.
"International Application Serial No. PCT/US2014/40860, International Search Report dated Oct. 9, 2014", 3 pgs.
"International Application Serial No. PCT/US2014/40860, Written Opinion dated Oct. 9, 2014", 6 pgs.
"International Application Serial No. PCT/US2017/047784, International Preliminary Report on Patentability dated Mar. 7, 2019", 9 pgs.
"International Application Serial No. PCT/US2017/047784, International Search Report dated Jan. 23, 2018", 8 pgs.
"International Application Serial No. PCT/US2017/047784, Invitation to Pay Additional Fees and Partial Search Report dated Nov. 3, 2017", 11 pgs.
"International Application Serial No. PCT/US2017/047784, Written Opinion dated Jan. 23, 2018", 7 pgs.
"International Application Serial No. PCT/US2018/012930, International Preliminary Report on Patentability dated Jul. 25, 2019", 7 pgs.
"International Application Serial No. PCT/US2018/012930, International Search Report dated Jun. 26, 2018", 4 pgs.
"International Application Serial No. PCT/US2018/012930, Written Opinion dated Jun. 26, 2018", 7 pgs.
"International Application Serial No. PCT/US2018/026186, International Search Report dated Jun. 28, 2018", 6 pgs.
"International Application Serial No. PCT/US2018/026186, Written Opinion dated Jun. 28, 2018", 6 pgs.
"Japanese Application Serial No. 2016-503289, Examiners Decision of Final Refusal dated Jan. 9, 2018", (English Translation), 5 pgs.
"Japanese Application Serial No. 2016-503289, Office Action dated Jun. 5, 2017", with English translation, 7 pgs.
"Japanese Application Serial No. 2016-503289, Response filed Nov. 2, 2017 to Office Action dated Jun. 5, 2017", w/ claims in English, 9 pgs.
Blum, David, et al., "Systems and Methods for Closed-Loop Determination of Stimulation Parameter Settings for an Electrical Simulation System", U.S. Appl. No. 62/408,620, filed Oct. 14, 2016.
Dayan, Peter, et al., "Theoretical Neuroscience", Chapter 7 (MIT Press 2001) 54 pages.
De Hemptinne, Coralie, et al., "Exaggerated phase-amplitude coupling in the primary motor cortex in Parkinson disease", PNAS, vol. 110, No. 12, (Mar. 19, 2013), 4780-4785.
Gerstner, Wulfram, et al., "Spiking Neuron Models, Single Neurons, Populations, Plasticity", Chapter 4 (Cambridge University Press), 66 pages 2002.
Hammond, Constance, "Pathological synchronization in Parkinson's disease: networks, models and treatments", Trends in Neuroscience, vol. 30, No. 7, (May 25, 2007), 357-364.
Lee, Dongchul, et al., "Method for Selectively Modulating Neural Elements in the Dorsal Horn", U.S. Appl. No. 13/843,102, filed Mar. 15, 2013.
Steinke, G. Karl, et al., "Systems and Methods for Making and Using Improved Contact Arrays for Electrical Stimulation Systems", U.S. Appl. No. 62/113,291, filed Feb. 6, 2015.
Tass, P.A., "Desynchronization by Means of a Coordinated Reset of Neural Sub-Populations", Progress of Theoretical Physics Supplement, No. 150, 281-296 (2003).
Tort, Adriano, et al., "Measuring Phase-Amplitude Coupling Between Neuronal Oscillations of Different Frequencies", J Neurophysiol 104, (2010), 1195-1210.
Vansickle, Dennis Allen, et al., "Neuromodulation System And Method For Transitioning Between Programming Modes", U.S. Appl. No. 14/214,752, filed Mar. 15, 2014.
Zhang, T.C., et al., "Modeling effects of spinal cord stimulation on wide-dynamic range dorsal horn neurons: influence of stimulation frequency and GABAergic inhibition", J Neurophysiol 112: 552-567, 2014.
"U.S. Appl. No. 15/865,805, Amendment Filed Jul. 6, 2020", 8 pgs.
"U.S. Appl. No. 15/865,805, Appeal Brief filed Jan. 12, 2022", 22 pgs.
"U.S. Appl. No. 15/865,805, Appeal Brief filed Jan. 12, 2022", 18 pgs.
"U.S. Appl. No. 15/865,805, Examiner Interview Summary dated Jan. 14, 2021", 2 pgs.
"U.S. Appl. No. 15/865,805, Examiner Interview Summary dated Jun. 14, 2021", 2 pgs.
"U.S. Appl. No. 15/865,805, Examiner Interview Summary dated Sep. 24, 2020", 4 pgs.
"U.S. Appl. No. 15/865,805, Examiner's Answer dated Mar. 15, 2022", 10 pgs.
"U.S. Appl. No. 15/865,805, Final Office Action dated Apr. 19, 2021", 16 pgs.
"U.S. Appl. No. 15/865,805, Non Final Office Action dated Jul. 14, 2020", 12 pgs.
"U.S. Appl. No. 15/865,805, Non Final Office Action dated Sep. 3, 2021", 17 pgs.
"U.S. Appl. No. 15/865,805, Non Final Office Action dated Nov. 20, 2020", 14 pgs.
"U.S. Appl. No. 15/865,805, Response filed Feb. 22, 2021 to Non Final Office Action dated Nov. 20, 2020", 10 pgs.
"U.S. Appl. No. 15/865,805, Response filed Jun. 29, 2021 to Final Office Action dated Apr. 19, 2021", 9 pgs.
"U.S. Appl. No. 15/865,805, Response filed Sep. 29, 2020 to Non Final Office Action dated Jul. 14, 2020", 9 pgs.
"U.S. Appl. No. 15/865,805,Reply Brief filed May 12, 2022", 9 pgs.
"U.S. Appl. No. 15/945,028, Examiner Interview Summary dated Jan. 12, 2021", 3 pgs.
"U.S. Appl. No. 15/945,028, Examiner Interview Summary dated Jun. 29, 2020", 3 pgs.
"U.S. Appl. No. 15/945,028, Final Office Action dated Nov. 17, 2020", 10 pgs.
"U.S. Appl. No. 15/945,028, Notice of Allowance dated Feb. 19, 2021", 7 pgs.
"U.S. Appl. No. 15/945,028, Response filed Jan. 12, 2021 to Final Office Action dated Nov. 17, 2020", 10 pgs.
"U.S. Appl. No. 15/945,028, Response filed Jul. 6, 2020 to Non Final Office Action dated Apr. 6, 2020", 10 pgs.
"U.S. Appl. No. 15/945,995, Advisory Action dated Mar. 24, 2021", 3 pgs.
"U.S. Appl. No. 15/945,995, Examiner Interview Summary dated Mar. 2, 2021", 2 pgs.
"U.S. Appl. No. 15/945,995, Final Office Action dated Jan. 8, 2021", 18 pgs.
"U.S. Appl. No. 15/945,995, Non Final Office Action dated Apr. 23, 2021", 20 pgs.
"U.S. Appl. No. 15/945,995, Non Final Office Action dated Sep. 4, 2020", 13 pgs.
"U.S. Appl. No. 15/945,995, Response filed Feb. 25, 2021 to Final Office Action dated Jan. 8, 2021", 11 pgs.
"U.S. Appl. No. 15/945,995, Response filed Jun. 11, 2020 to Restriction Requirement dated Apr. 14, 2020", 8 pgs.
"U.S. Appl. No. 15/945,995, Response filed Oct. 6, 2020 to Non Final Office Action dated Sep. 4, 2020", 10 pgs.
"U.S. Appl. No. 15/945,995, Restriction Requirement dated Apr. 14, 2020", 7 pgs.
"U.S. Appl. No. 16/275,730, Final Office Action dated Oct. 22, 2021", 20 pgs.
"U.S. Appl. No. 16/275,730, Non Final Office Action dated Jun. 8, 2021", 17 pgs.
"U.S. Appl. No. 16/275,730, Response filed Sep. 2, 2021 to Non Final Office Action dated Jun. 8, 2021", 16 pgs.
"U.S. Appl. No. 16/275,892, 312 Amendment filed Mar. 18, 2022", 6 pgs.

(56) References Cited

OTHER PUBLICATIONS

"U.S. Appl. No. 16/275,892, Non Final Office Action dated Jul. 13, 2021", 12 pgs.
"U.S. Appl. No. 16/275,892, Notice of Allowance dated Dec. 22, 2021", 5 pgs.
"U.S. Appl. No. 16/275,892, PTO Response to Rule 312 Communication dated Mar. 25, 2022", 2 pgs.
"U.S. Appl. No. 16/275,892, Response filed May 25, 2021 to Restriction Requirement dated Mar. 31, 2021", 8 pgs.
"U.S. Appl. No. 16/275,892, Response filed Oct. 13, 2021 to Non Final Office Action dated Jul. 13, 2021", 13 pgs.
"U.S. Appl. No. 16/275,892, Restriction Requirement dated Mar. 31, 2021", 7 pgs.
"U.S. Appl. No. 17/712,988, Preliminary Amendment filed Apr. 5, 2022", 10 pgs.
"Australian Application Serial No. 2018251564, Response filed May 22, 2020 to First Examination Report dated Feb. 28, 2020", 15 pgs.
"Australian Application Serial No. 2018274915, Response Filed Jun. 25, 2020 to First Examination Report dated Feb. 25, 2020", 19 pgs.
"Australian Application Serial No. 2018274915, Response filed Nov. 30, 2020 to Subsequent Examiners Report dated Jul. 15, 2020", 18 pgs.
"Australian Application Serial No. 2018274915, Subsequent Examiners Report dated Jul. 15, 2020", 4 pgs.
"Australian Application Serial No. 2021201819, First Examination Report dated Feb. 9, 2022", 3 pgs.
"Australian Application Serial No. 2021201819, Response filed Jul. 15, 2022 to First Examination Report dated Feb. 9, 2022", 24 pgs.
"Australian Application Serial No. 2021201819, Subsequent Examiners Report dated Jul. 18, 2022", 2 pgs.
"Chinese Application Serial No. 201710757674.X, Office Action dated May 6, 2020", w/English translation, 34 pgs.
"Chinese Application Serial No. 201710757674.X, Response filed Sep. 9, 2020 to Office Action dated May 6, 2020", w/ English claims, 33 pgs.
"European Application Serial No. 18712707.1, Communication Pursuant to Article 94(3) EPC dated Jun. 23, 2022", 5 pgs.
"European Application Serial No. 18723100.6, Response to Communication Pursuant to Rules 161 and 162 filed May 19, 2020", 11 pgs.
"European Application Serial No. 19179413.0, Response filed Jun. 24, 2020 to Extended European Search Report dated Nov. 8, 2019", 14 pgs.
"European Application Serial No. 21169424.5, Communication Pursuant to Article 94(3) EPC dated May 13, 2022", 4 pgs.
"European Application Serial No. 21169424.5, Extended European Search Report dated Aug. 11, 2021", 7 pgs.
"European Application Serial No. 21169424.5, Response filed Mar. 22, 2022 to Extended European Search Report dated Aug. 11, 2021", 17 pgs.
Carcieri, Stephen, "Neurostimulation System and Method for Automatically Adjusting Stimulation and Reducing Energy Requirements Using Evoked Action Potential", U.S. Appl. No. 61/768,295, filed Feb. 22, 2013.
Lee, Dongchul, "Method for Selectively Modulating Nerve Endings in Spinal Cord", U.S. Appl. No. 61/703,195, filed Sep. 19, 2012.
Lee, Dongchul, et al., "Neurostimulation System for Defining a Generalized Ideal Multipole Configuration", U.S. Appl. No. 61/452,965, filed Mar. 15, 2011.
Magteld, Zeitler, et al., "Augmented brain function by coordinated reset stimulation with slowly varying sequences", Frontiers in systems neuroscience vol. 9 49, (Mar. 31, 2015).
Maling, N, et al., "Chapter 5—Local Field Potential Analysis for Closed-Loop Neuromodulation,", Editors): Ahmed El Hady, Closed Loop Neuroscience, Academic Press, <http://www.sciencedirect.com/science/article/pii/B9780128024522000Q56>, (2016), 67-80.
Popovych, Oleksandr, et al., "Desynchronizing electrical and sensory coordinated reset neuromodulation", Frontiers in Human Neuroscience, vol. 6, <https://www.frontiersin.org/article/10.3389/fnhum.2012.00058>, (2012).
Rao, Prakash, et al., "Technique for Linking Electrodes Together During Programming of Neurostimulation System", U.S. Appl. No. 61/561,760, filed Nov. 18, 2011.
Ryan, T Canolty, et al., "The functional role of cross-frequency coupling", Trends in cognitive sciences vol. 14, (2010), 506-15.
Sohelia, Samiee, "Phase-amplitude coupling", <https://web.archive.org/web/20170325185416/https://neuroimage.usc.edu/brainstorm/Tutorials/TutPac>, (Dec. 28, 2020).
Steinke, G. Karl, et al., "Systems and Methods for Making and Using Improved Contact Arrays for Electrical Stimulation Systems", U.S. Appl. No. 62/113,291, filed Feb. 6, 2015, 45 pgs.
Vansickle, Dennis Allen, "Systems And Methods For Delivering Sub-Threshold Therapy To A Patient", U.S. Appl. No. 61/801,917, filed Mar. 15, 2013.

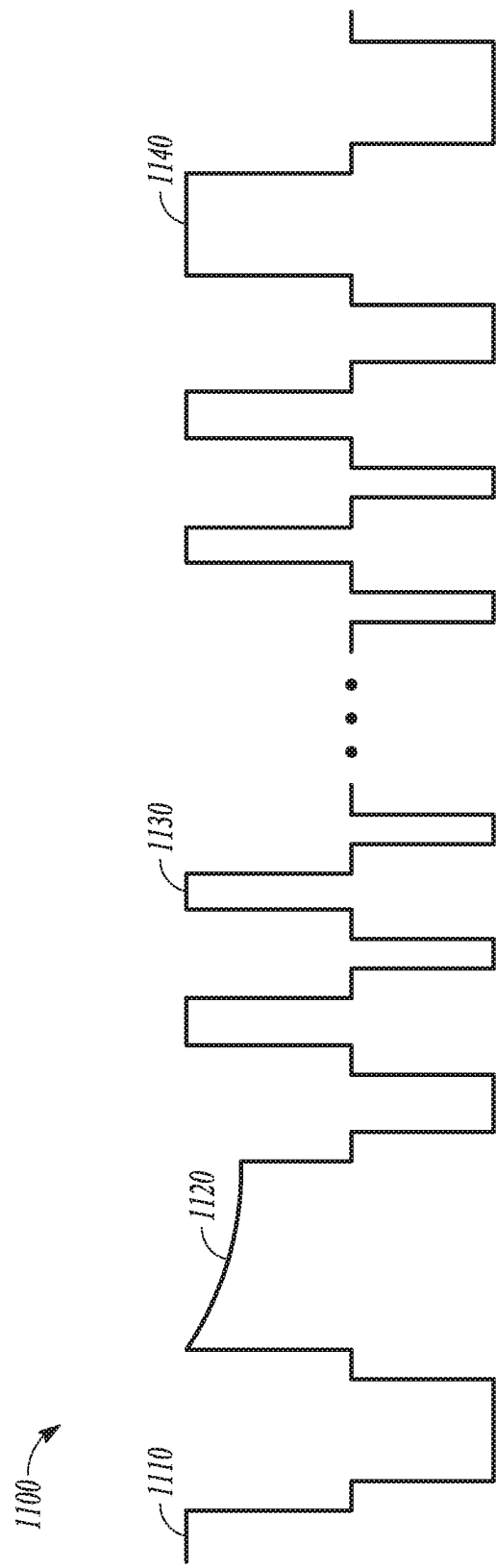

SYSTEMS AND METHODS FOR DELIVERING SPINAL CORD STIMULATION THERAPY

CLAIM OF PRIORITY

This application is a continuation of U.S. application Ser. No. 15/681,765, filed Aug. 21, 2017, which claims the benefit of priority under 35 U.S.C. § 119(e) of U.S. Provisional Patent Application Ser. No. 62/378,007, filed on Aug. 22, 2016, which is herein incorporated by reference in its entirety.

TECHNICAL FIELD

This document relates generally to medical devices, and more particularly, to systems, devices and methods for delivering neural modulation.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

Neurostimulation energy may be delivered using electrical energy that may be controlled using stimulation parameters that specify spatial (where to stimulate), temporal (when to stimulate), and informational (stimulation patterns directing the nervous system to respond as desired) aspects of a pattern of neurostimulation pulses.

SUMMARY

Many current neurostimulation systems are programmed to deliver periodic pulses with one or a few uniform waveforms continuously or in bursts. However, the human nervous systems use neural signals having much more sophisticated patterns to communicate various types of information, including sensations of pain, pressure, temperature, etc. The nervous system may interpret an artificial stimulation with a simple pattern of stimuli as an unnatural phenomenon, and respond with an unintended and undesirable sensation and/or movement. For example, some neurostimulation therapies are known to cause paresthesia and/or vibration of non-targeted tissue or organ.

Recent research has shown that the efficacy and efficiency of certain neurostimulation therapies can be improved, and their side-effects can be reduced, by using patterns of neurostimulation pulses that emulate natural patterns of neural signals observed in the human body. Various examples disclosed herein treat a patient with a neuromodulation system that delivers a supra-perception therapy such as therapy that causes paresthesia. The neuromodulation system delivers an electrical waveform to electrodes implanted within the patient, where the electrical waveform includes a distribution of frequencies for providing the paresthesia therapy.

An example, (e.g., "Example 1") of subject matter (e.g., a neuromodulation system) may include a first storage device configured to store a waveform pattern having multiple frequencies, modulation circuitry configured to provide paresthesia by delivering an electrical waveform to a patient, the electrical waveform including the stored waveform pattern, the electrical waveform having a duration and having a distribution of frequencies in the range of 0.001 kHz to 20 kHz, and wherein the patient continuously experiences paresthesia and analgesia for the duration of the electrical waveform.

In Example 2, the subject matter of Example 1 may optionally be configured such that the waveform pattern includes at least one frequency above 0.001 kHz and below 2.0 kHz and at least one frequency above 2.0 kHz and below 20 kHz.

In Example 3, the subject matter of Example 1 may optionally be configured such that the waveform pattern includes a first group of frequencies having an average frequency above 0.001 kHz and below 2.0 kHz and a second group of frequencies having an average frequency above 2.0 kHz and below 20 kHz.

In Example 4, the subject matter of Example 1 may optionally be configured such that the waveform pattern includes a frequency modulated waveform at a frequency modulation rate to vary a frequency of the waveform pattern between a lower frequency limit and a higher frequency limit to provide the distribution of frequencies in the range of 0.001 kHz to 20 kHz.

In Example 5, the subject matter of Example 4 may optionally be configured such that the lower frequency limit is within a range extending from 0.001 kHz to 2.0 kHz, and the upper frequency limit is within a range extending from 2.0 kHz to 20 kHz.

An example, (e.g., "Example 6") of subject matter (e.g., a system) may include a lead system including electrodes configured to be implanted in an epidural space, including electrodes configured for use to stimulate a first region and electrodes configured for use to stimulate a second region, and modulation circuitry configured to provide stimulation to a patient, wherein the modulation circuitry is configured to use the lead system to deliver a first electrical stimulation to the first region, and use the lead system to deliver a second electrical stimulation to the second region.

In Example 7, the subject matter of Example 6 may optionally be configured such that the first electrical stimulation has a first frequency of less than 2.0 kHz and the first region is selected based on patient feedback to provide paresthesia to treat pain and wherein the second electrical stimulation is sub-perception stimulation and has a second frequency of less than 1.5 kHz, and wherein the first region includes at least one of the T6, T7, T8, and T9 vertebrae, and wherein the second region includes at least one of the T8, T9, T10 vertebrae.

In Example 8, the subject matter of Example 7 may optionally be configured such that the first electrical stimulation has a first frequency of less than 1.5 kHz.

In Example 9, the subject matter of Example 6 may optionally be configured such that the first electrical stimulation is sub-perception and has a first frequency of less than 1.5 kHz and the first region includes at least one of the T6, T7, T8, and T9 vertebrae, and wherein the second electrical stimulation is sub-perception stimulation and has a second frequency of less than 1.5 kHz, and wherein the second region includes at least one of the T8, T9, T10 vertebrae.

In Example 10, the subject matter of Example 9 may optionally be configured such that the first electrical stimulation has a first frequency of less than 1.0 kHz and the second electrical stimulation has a second frequency of greater than 1.0 kHz and less than 1.5 kHz.

In Example 11, the subject matter of Example 9 may optionally be configured such that the first region includes at least one of the T7 and T8 vertebrae.

In Example 12, the subject matter of Example 9 may optionally be configured such that the second region includes at least one of the T8 and T9 vertebrae.

In Example 13, the subject matter of Example 6 may optionally be configured such that the modulation circuitry is further configured to apply a dorsal column (DC) modulation field to modulate DC fibers, the first region includes one of DC fibers or DH fibers, and the first electrical stimulation has a first frequency of less than or equal to 2 kHz, and wherein the modulation circuitry is further configured to apply a DH modulation field to modulate DH fibers, the second region includes the other of DC fibers or DH fibers, and wherein the second electrical stimulation has a second frequency of less than or equal to 2 kHz.

In Example 14, the subject matter of Example 13 may optionally be configured such that the first electrical stimulation has a first frequency of less than 1.5 kHz and the first electrical stimulation provides a sub-perception therapy.

In Example 15, the subject matter of Example 14 may optionally be configured such that the second electrical stimulation has a second frequency of less than 1.5 kHz and the second electrical stimulation provides a sub-perception therapy.

An example, (e.g., "Example 16") of subject matter (e.g., a method) may include providing a paresthesia therapy to a patient using an implantable neuromodulation system, wherein providing the paresthesia therapy includes delivering to the patient an electrical waveform having a duration and a distribution of frequencies in the range of 0.001 kHz to 20 kHz, wherein the distribution of frequencies includes a first frequency group of one or more frequencies and a second frequency group of one or more frequencies, and wherein the patient continuously experiences paresthesia throughout the duration of the electrical waveform.

In Example 17, the subject matter of Example 16 may be optionally configured such that the first frequency group of one or more frequencies includes frequencies above 0.001 kHz and below 2.0 kHz and the second frequency group of one or more frequencies includes frequencies above 2.0 kHz and below 20 kHz.

In Example 18, the subject matter of Example 16 may be optionally configured such that the first frequency group of one or more frequencies has an average frequency in the range of 0.001 kHz and below 2.0 kHz and the second frequency group of one or more frequencies has an average frequency in the range of 2.0 kHz and below 20 kHz.

In Example 19, the subject matter of Example 16 may be optionally configured such that the electrical waveform includes a frequency modulated waveform having a frequency that varies at a frequency modulation rate between a lower frequency limit and a higher frequency limit to provide the distribution of frequencies in the range of 0.001 kHz to 20 kHz.

In Example 20, the subject matter of Example 19 may be optionally configured such that the lower frequency limit is within a range extending from 0.001 kHz to 2.0 kHz, and the upper frequency limit is within a range extending from 2.0 kHz to 20 kHz.

In Example 21, the subject matter of Example 20 may be optionally configured such that the lower frequency limit is within a range extending from 1.0 kHz to 1.5 kHz, and the upper frequency limit is within a range extending from 2.0 kHz to 10 kHz.

An example, (e.g., "Example 22") of subject matter (e.g., a neuromodulation system) may include a first storage device configured to store a waveform pattern having multiple frequencies, modulation circuitry configured to provide paresthesia by delivering an electrical waveform to a patient, the electrical waveform including the stored waveform pattern, the electrical waveform having a duration and having a distribution of frequencies in the range of 0.001 kHz to 20 kHz, and wherein the patient continuously experiences paresthesia and analgesia for the duration of the electrical waveform.

In Example 23, the subject matter of Example 22 may be optionally configured such that the waveform pattern includes at least one frequency above 0.001 kHz and below 2.0 kHz and at least one frequency above 2.0 kHz and below 20 kHz.

In Example 24, the subject matter of Example 22 may be optionally configured such that the waveform pattern includes a first group of frequencies having an average frequency above 0.001 kHz and below 2.0 kHz and a second group of frequencies having an average frequency above 2.0 kHz and below 20 kHz.

In Example 25, the subject matter of Example 22 may be optionally configured such that the waveform pattern includes a frequency modulated waveform at a frequency modulation rate to vary a frequency of the waveform pattern between a lower frequency limit and a higher frequency limit to provide the distribution of frequencies in the range of 0.001 kHz to 20 kHz.

In Example 26, the subject matter of Example 25 may be optionally configured such that the lower frequency limit is within a range extending from 0.001 kHz to 2.0 kHz, and the upper frequency limit is within a range extending from 2.0 kHz to 20 kHz.

An example, (e.g., "Example 27") of subject matter (e.g., a system) may include a lead system including electrodes configured to be implanted in an epidural space, including electrodes configured for use to stimulate a first region and electrodes configured for use to stimulate a second region, and modulation circuitry configured to provide stimulation to a patient, wherein the modulation circuitry is configured to use the lead system to deliver a first electrical stimulation to the first region, and use the lead system to deliver a second electrical stimulation to the second region.

In Example 28, the subject matter of Example 27 may be optionally configured such that the first electrical stimulation has a first frequency of less than 2.0 kHz and the first region is selected based on patient feedback to provide paresthesia to treat pain and wherein the second electrical stimulation is sub-perception stimulation and has a second frequency of less than 1.5 kHz, and wherein the first region includes at least one of the T6, T7, T8, and T9 vertebrae, and wherein the second region includes at least one of the T8, T9, T10 vertebrae.

In Example 29, the subject matter of Example 28 may be optionally configured such that the first electrical stimulation has a first frequency of less than 1.5 kHz.

In Example 30, the subject matter of Example 27 may be optionally configured such that the first electrical stimulation is sub-perception and has a first frequency of less than 1.5 kHz and the first region includes at least one of the T6, T7, T8, and T9 vertebrae, and wherein the second electrical stimulation is sub-perception stimulation and has a second frequency of less than 1.5 kHz, and wherein the second region includes at least one of the T8, T9, T10 vertebrae.

In Example 31, the subject matter of Example 30 may be optionally configured such that the first electrical stimulation has a first frequency of less than 1.0 kHz and the second electrical stimulation has a second frequency of greater than 1.0 kHz and less than 1.5 kHz.

In Example 32, the subject matter of Example 30 may be optionally configured such that the first region includes at least one of the T7 and T8 vertebrae.

In Example 33, the subject matter of Example 30 may be optionally configured such that the second region includes at least one of the T8 and T9 vertebrae.

In Example 34, the subject matter of Example 27 may be optionally configured such that the modulation circuitry is further configured to apply a dorsal column (DC) modulation field to modulate DC fibers, the first region includes one of DC fibers or DH fibers, and the first electrical stimulation has a first frequency of less than or equal to 2 kHz, and wherein the modulation circuitry is further configured to apply a DH modulation field to modulate DH fibers, the second region includes the other of DC fibers or DH fibers, and wherein the second electrical stimulation has a second frequency of less than or equal to 2 kHz.

In Example 35, the subject matter of Example 34 may be optionally configured such that the first electrical stimulation has a first frequency of less than 1.5 kHz and the first electrical stimulation provides a sub-perception therapy.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 11 illustrates an example of a waveform for providing a paresthesia therapy

DETAILED DESCRIPTION

Various examples disclosed herein describe treating a patient with a neuromodulation system that delivers a supra-perception therapy such as therapy that causes paresthesia.

Figure 1:
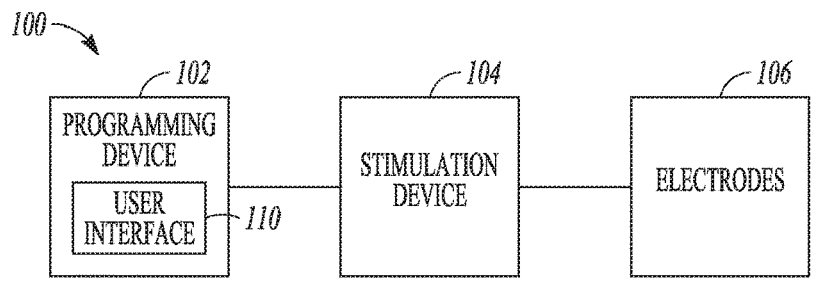
FIG. 1 illustrates an example of a neurostimulation system.

FIG. 1 illustrates an embodiment of a neurostimulation system 100. In an example, neurostimulation system 100 includes electrodes 106, a stimulation device 104, and a programming device 102. Electrodes 106 may be configured to be placed on or near one or more neural targets in a patient. Stimulation device 104 may be configured to be electrically connected to electrodes 106 and deliver neurostimulation energy, such as in the form of electrical pulses, to the one or more neural targets though electrodes 106. The delivery of the neurostimulation may be controlled by using a plurality of stimulation parameters, such as stimulation parameters specifying a waveform shape such as, but not limited to, a pattern of the electrical pulses and a selection of electrodes through which each of the electrical pulses is delivered. In an example, at least some parameters of the plurality of stimulation parameters are programmable by a user, such as a physician or other caregiver who treats the patient using system 100. Programming device 102 may provide the user with accessibility to the user-programmable parameters. In an example, programming device 102 is configured to be communicatively coupled to stimulation device via a wired or wireless link.

In an example, programming device 102 includes a user interface that allows the user to set and/or adjust values of the user-programmable parameters by creating and/or editing graphical representations of various waveforms. Such waveforms may include different waveform shapes. The waveform shapes may include regular shapes (e.g. square, sinusoidal, triangular, saw tooth, and the like) or irregular shapes. The waveform shapes may include regular or irregular patterns. The waveform shapes may be similar to analog signals or may be similar to digitized signals. By way of example and not limitation, the waveforms may include a pattern of temporal waveform segments, which may include a pattern of neurostimulation pulses, to be delivered to the patient. The waveform segments may function as waveform building blocks which may be concatenated in various patterns to form larger a larger waveform. A waveform building block may contain a selected distribution of frequencies desirable for a therapy (e.g. therapy where a patient continuously experiences paresthesia and analgesia for the duration of the electrical waveform). Some embodiments may use two or more building blocks to provide a selected distribution of frequencies desirable for a therapy. Some embodiments may use waveforms that are formed without pulses. Examples of such waveform building blocks include pulses, bursts each including a group of the pulses, trains each including a group of the bursts, and sequences each including a group of the pulses, bursts, and trains, as further discussed below. In an example, programming device 102 allows the user to edit existing waveform building blocks, create new waveform building blocks, import waveform building blocks created by other users, and/or export waveform building blocks to be used by other users. The user may also be allowed to define an electrode selection specific to each waveform building block. In an example, the user interface includes a user interface 110. In an example, user interface 110 may include a GUI or any other type of user interface accommodating various functions including waveform composition as discussed in this document.

Figure 2:
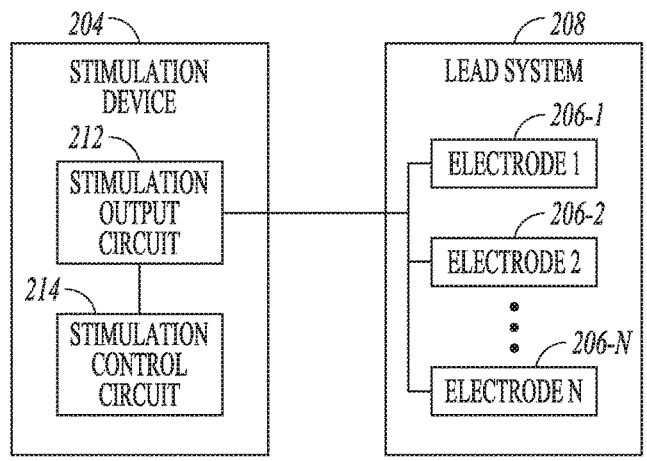
FIG. 2 illustrates an example of a stimulation device and a lead system.

FIG. 2 illustrates an embodiment of a stimulation device 204 and a lead system 208, such as may be implemented in neurostimulation system 100. In an example, stimulation device 204 includes a stimulation output circuit 212 and a stimulation control circuit 214. Stimulation output circuit 212 may produce and deliver neurostimulation pulses. Stimulation control circuit 214 may control the delivery of the neurostimulation pulses using the plurality of stimulation parameters, which specifies a pattern of the neurostimulation pulses. Lead system 208 may include one or more leads each configured to be electrically connected to stimulation device 204 and a plurality of electrodes 206 distributed in the one or more leads. The plurality of electrodes 206 may include electrode 206-1, electrode 206-2, . . . electrode 206-N, each a single electrically conductive contact providing for an electrical interface between stimulation output circuit 212 and tissue of the patient, where N≥2. The neurostimulation pulses may be delivered from stimulation output circuit 212 through a set of electrodes selected from electrodes 206.

In an example, the number of leads and the number of electrodes on each lead depend on, for example, the distribution of target(s) of the neurostimulation and the need for controlling the distribution of electric field at each target. In one example, lead system 208 includes 2 leads each having 8 electrodes.

Figure 3:
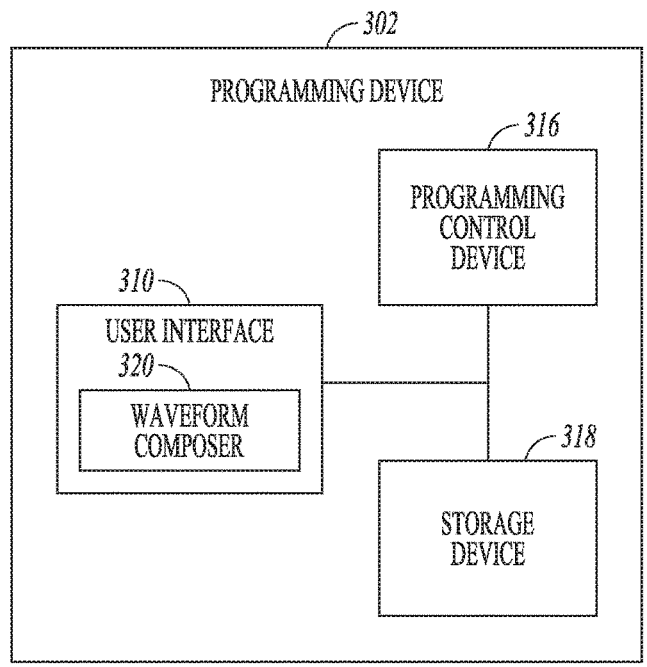
FIG. 3 illustrates an example of a programming device.

FIG. 3 illustrates an embodiment of a programming device 302, such as may be implemented in neurostimulation system 100. In an example, programming device 302 includes a storage device 318, a programming control circuit 316, and a user interface 310. Storage device 318 may store a plurality of temporal waveform segments as waveform building blocks. The temporal waveform segments may include pulses and may include other waveform shapes. Programming control circuit 316 may generate the plurality of stimulation parameters that controls the delivery of the neurostimulation according to the pattern of the neurostimulation pulses. User interface 310 may allow the user to compose the waveform building blocks and compose the pattern of the neurostimulation pulses using one or more waveform building blocks selected from the plurality of waveform building blocks.

In an example, user interface 310 includes a waveform composer 320 that allows the user to manage the waveform building blocks, including creating and importing waveform building blocks to be added to the waveform building blocks stored in storage device 318, exporting waveform building blocks selected from the waveform building blocks stored in storage device 318, and editing each of the waveform building blocks. In an example, user interface 310 includes a GUI that allows for graphical editing of each of the waveform building blocks. In an example, waveform composer 320 may be configured to allow the user to compose a shape of the waveform. In an example, the waveform composer 320 may be configured to allow the user to compose a pattern of neurostimulation pulses to be delivering to the patent using stimulation device 104 using waveform building blocks such as pulses, bursts each including a group of the pulses, trains each including a group of the bursts, and/or sequences each including a group of the pulses, bursts, and trains. In an example, waveform composer 320 allows the user to create each waveform building block using one or more waveform building blocks stored in storage device 318 as templates. In an example, waveform composer 320 allows each newly created waveform building block to be saved as additional waveform building block stored in storage device 318.

In an example, user interface 310 includes a touchscreen. In an example, user interface 310 includes any type of presentation device, such as interactive or non-interactive screens, and any type of user input devices that allow the user to edit the waveforms or building blocks and schedule the programs, such as touchscreen, keyboard, keypad, touchpad, trackball, joystick, and mouse. In an example, circuits of neurostimulation 100, including its various embodiments discussed in this document, may be implemented using a combination of hardware and software. For example, the circuit of user interface 100, stimulation control circuit 214, and programming control circuit 316, including their various embodiments discussed in this document, may be implemented using an application-specific circuit constructed to perform one or more particular functions or a general-purpose circuit programmed to perform such function(s). Such a general-purpose circuit may include, but is not limited to, a microprocessor or a portion thereof, a microcontroller or portions thereof, and a programmable logic circuit or a portion thereof.

Figure 4:
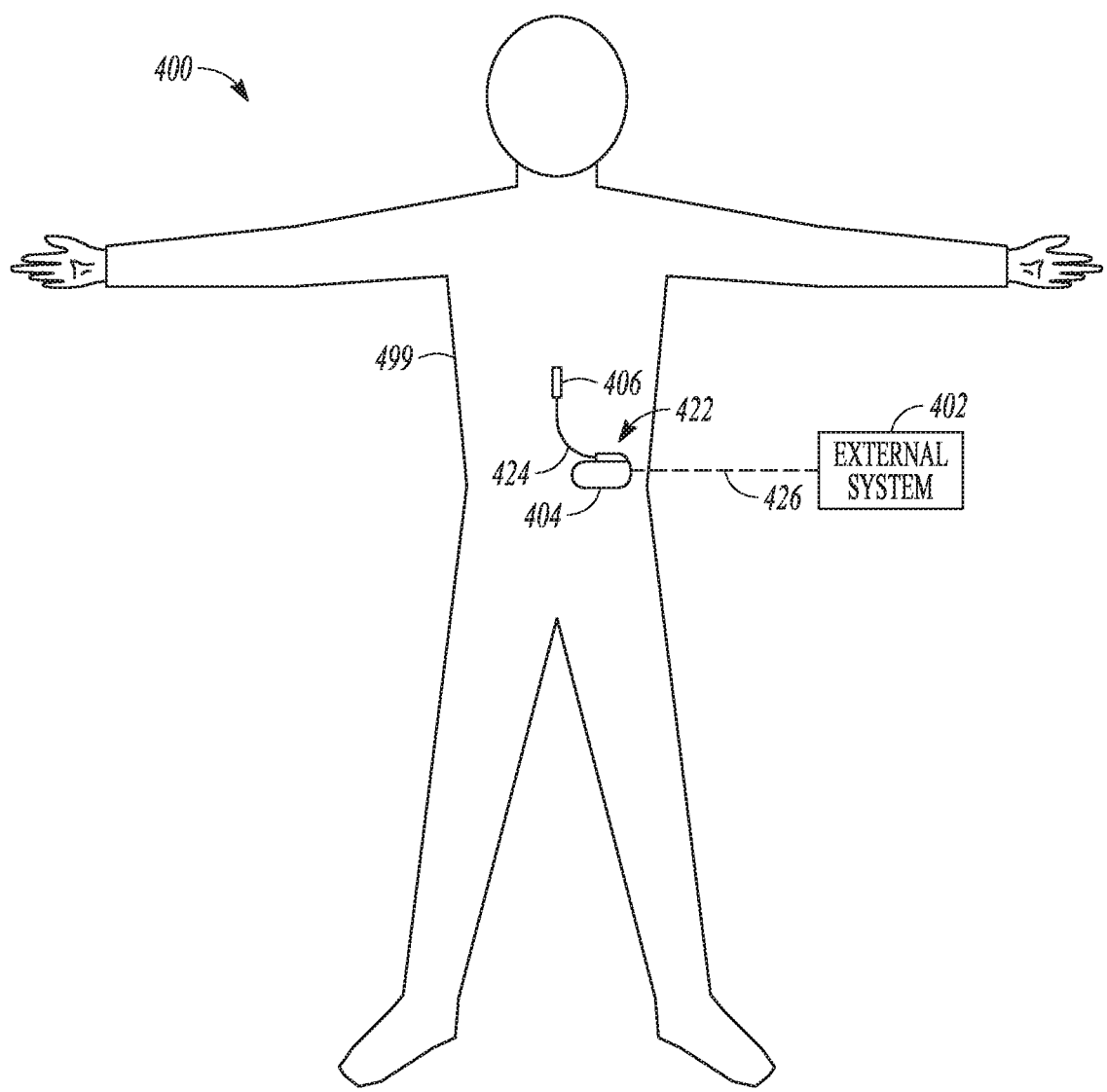
FIG. 4 illustrates an example of an implantable neurostimulation system.

FIG. 4 illustrates an implantable neurostimulation system 400 and portions of an environment in which system 400 may be used. In an example, system 400 includes an implantable system 422, an external system 402, and a telemetry link 426 providing for wireless communication between implantable system 422 and external system 402. In an example, implantable system 422 is illustrated in FIG. 4 as being implanted in the patient's body 499.

In an example, implantable system 422 includes an implantable stimulator (also referred to as an implantable pulse generator, or IPG) 404, a lead system 424, and electrodes 406, which represent an embodiment of stimulation device 204, lead system 208, and electrodes 206, respectively. In an example, external system 402 represents an example of programming device 302. In an example, external system 402 includes one or more external (non-implantable) devices each allowing the user and/or the patient to communicate with implantable system 422. In some examples, external 402 includes a programming device intended for the user to initialize and adjust settings for implantable stimulator 404 and a remote control device intended for use by the patient. For example, the remote control device may allow the patient to turn implantable stimulator 404 on and off and/or adjust certain patient-programmable parameters of the plurality of stimulation parameters.

In an example, the sizes and shapes of the elements of implantable system 422 and their location in body 499 are illustrated by way of example and not by way of restriction. In an example, an implantable system is discussed as a specific application of the programming according to various embodiments of the present subject matter. In various examples, the present subject matter may be applied in programming any type of stimulation device that uses electrical pulses as stimuli, regarding less of stimulation targets in the patient's body and whether the stimulation device is implantable.

Figure 5:
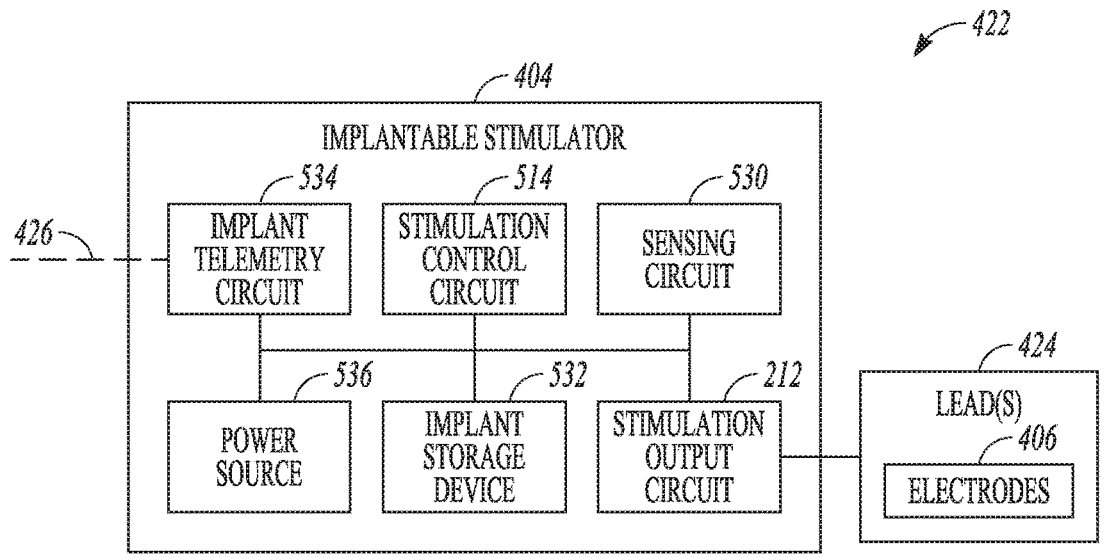
FIG. 5 illustrates an example of an implantable stimulator and one or more leads of an implantable neurostimulation system.

FIG. 5 illustrates an embodiment of implantable stimulator 404 and one or more leads 424 of an implantable neurostimulation system, such as implantable system 422. In an example, implantable stimulator 404 may include a sensing circuit 530 that is optional and required only when the stimulator has a sensing capability, stimulation output circuit 212, a stimulation control circuit 514, an implant storage device 532, an implant telemetry circuit 534, and a power source 536. Sensing circuit 530 may sense one or more physiological signals for purposes of patient monitoring and/or feedback control of the neurostimulation. Examples of the one or more physiological signals includes neural and other signals each indicative of a condition of the patient that is treated by the neurostimulation and/or a response of the patient to the delivery of the neurostimulation. Stimulation output circuit 212 may be electrically connected to electrodes 406 through lead 424, and delivers the neurostimulation through a set of electrodes selected from electrodes 406. Stimulation control circuit 514 may represent an example of stimulation control circuit 214 and control the delivery of the neurostimulation using the plurality of stimulation parameters specifying the pattern of the neurostimulation. In one example, stimulation control circuit 514 controls the delivery of the neurostimulation using the one or more sensed physiological signals. Implant telemetry circuit 534 may provide implantable stimulator 404 with wireless communication with another device such as a device of external system 402, including receiving values of the plurality of stimulation parameters from external system 402. Implant storage device 532 may store values of the plurality of stimulation parameters. Power source 536 may provide implantable stimulator 404 with energy for its operation. In one example, power source 536 includes a battery. In one example, power source 536 includes a rechargeable battery and a battery charging circuit for charging the rechargeable battery. Implant telemetry circuit 534 may also function as a power receiver that receives power transmitted from external system 402 through an inductive couple.

In various examples, sensing circuit 530 (if included), stimulation output circuit 212, stimulation control circuit 514, implant telemetry circuit 534, implant storage device 532, and power source 536 are encapsulated in a hermetically sealed implantable housing. In various examples, lead (s) 424 are implanted such that electrodes 406 are places on and/or around one or more targets to which the neurostimulation pulses are to be delivered, while implantable stimulator 404 is subcutaneously implanted and connected to lead(s) 424 at the time of implantation.

Figure 6:
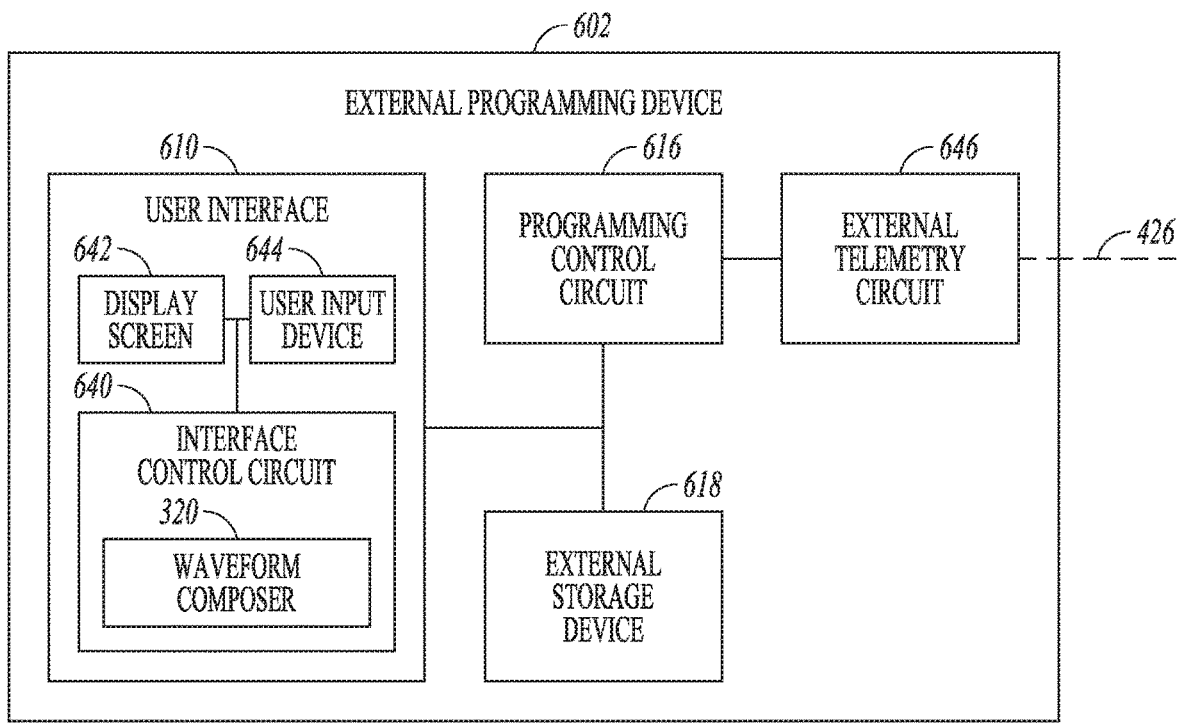
FIG. 6 illustrates an example of an external programming device of an implantable neurostimulation system.

FIG. 6 illustrates an embodiment of an external programming device 602 of an implantable neurostimulation system, such as external system 402. External programming device 602 may represent an example of programming device 302, and may include an external telemetry circuit 646, an external storage device 618, a programming control circuit 616, and a user interface 610.

In an example, external telemetry circuit 646 provides external programming device 602 with wireless communication with another device such as implantable stimulator 404 via telemetry link 426, including transmitting the plurality of stimulation parameters to implantable stimulator 404. In one example, external telemetry circuit 646 also transmits power to implantable stimulator 404 through the inductive couple.

In an example, external storage device 618 stores a plurality of waveform building blocks each selectable for use as a temporal segment of the neurostimulation waveform. In various examples, each waveform building block of the plurality of waveform building blocks includes one or more pulses of the neurostimulation pulses, and may include one or more other waveform building blocks of the plurality of waveform building blocks. Examples of such waveforms include pulses, bursts each including a group of the pulses, trains each including a group of the bursts, and sequences each including a group of the pulses, bursts, and trains. External storage device 618 may also store a plurality of stimulation fields. Each waveform building block of the plurality of waveform building blocks may be associated with one or more fields of the plurality of stimulation fields. Each field of the plurality of stimulation fields may be defined by one or more electrodes of the plurality of electrodes through which a pulse of the neurostimulation pulses is delivered and a current distribution of the pulse over the one or more electrodes.

In an example, programming control circuit 616 generates a plurality of stimulation parameters, which are to be transmitted to implantable stimulator 404, according to the pattern of the neurostimulation pulses. The pattern may be defined using one or more waveform building blocks selected from the plurality of waveform building blocks stored in external storage device 618. In various examples, programming control circuit 616 checks values of the plurality of stimulation parameters against safety rules to limit these values within constraints of the safety rules. In one example, the safety rules are heuristic rules.

In an example, user interface 610 allows the user to define the pattern of neurostimulation pulses and perform various other monitoring and programming tasks. In one example, user interface 610 includes a GUI. User interface 610 may include a display screen 642, a user input device 644, and an interface control circuit 640. Display screen 642 may include any type of interactive or non-interactive screens, and user input device 644 may include any type of user input devices that supports the various functions discussed in this document, such as touchscreen, keyboard, keypad, touchpad, trackball, joystick, and mouse. In one example, user interface 610 includes a GUI that has an interactive screen for displaying a graphical representation of a waveform building block and allows the user to adjust the waveform building block by graphically editing the waveform building block. User interface 610 may also allow the user to perform any other functions discussed in this document where graphical editing is suitable as may be appreciated by those skilled in the art.

In an example, interface control circuit 640 controls the operation of user interface 610 including responding to various inputs received by user input device 644 and defining the one or more stimulation waveforms. Interface control circuit 640 includes waveform composer 320.

In an example, external programming device 602 has operation modes including a composition mode and a real-time programming mode. In the composition mode (also known as the pulse pattern composition mode), user interface 610 may be activated, while programming control circuit 616 may be inactivated. In an example, programming control circuit 616 does not dynamically update values of the plurality of stimulation parameters in response to any change in the one or more stimulation waveforms. In the real-time programming mode, both user interface 610 and programming control circuit 616 may be activated. Programming control circuit 616 may dynamically update values of the plurality of stimulation parameters in response to changes in the set of one or more stimulation waveforms, and transmit the plurality of stimulation parameters with the updated values to implantable stimulator 404.

Figure 7:
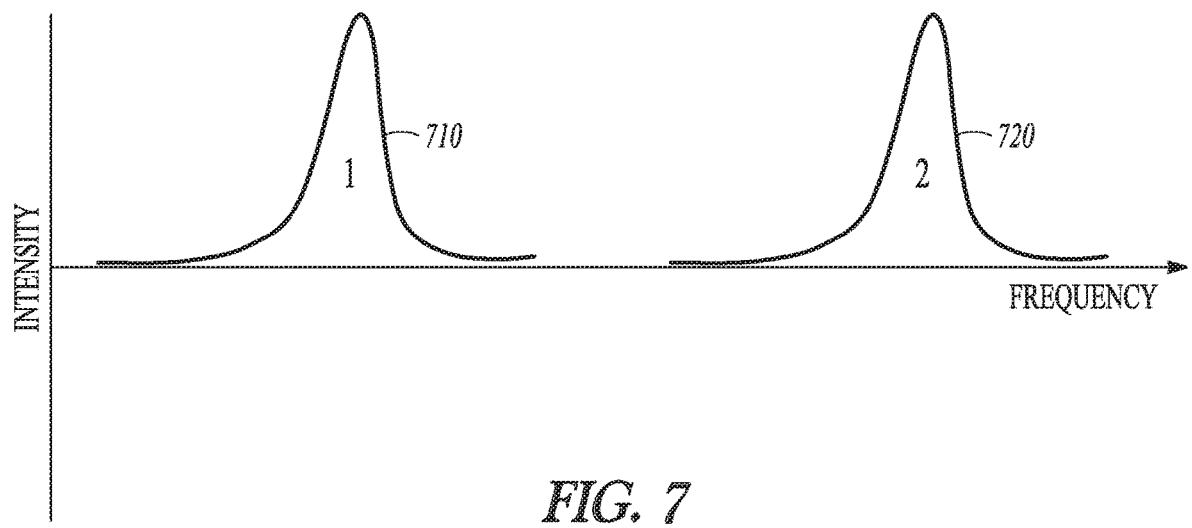
FIG. 7 illustrates an example of a distribution of frequencies for providing a paresthesia therapy.

FIG. 7 illustrates an example of a frequency distribution for an electrical waveform having a distribution of frequencies for providing used to provide a paresthesia therapy. In an example, the electrical waveform having the distribution of frequencies may be delivered to one or more neural targets through implanted electrodes to provide a continuous paresthesia for a duration of the electrical waveform. In an example, the electrical waveform may include a first frequency group 710 and a second frequency group 720. It is noted that the frequency distribution is an illustration, and that the electrical waveform may include frequencies between the first and second group. Further, the frequency distribution may be provided using one building block for a temporal waveform segment, or may be provided using two or more building blocks arranged to provide concatenated temporal waveform segments. The first frequency group 710 and the second frequency group 720 may include frequencies in the range of 0.001 kHz to 20 kHz. In an example, the first frequency group 710 includes frequencies below 2.0 kHz and the second frequency group 720 includes frequencies above 2.0 kHz. In an example, the first frequency group 710 has an average frequency in the range of 0.001 kHz to 2.0 kHz and the second frequency group 720 has an average frequency in the range of 2.0 kHz to 20 kHz. In an example, the first frequency group 710 includes frequencies below 0.1 kHz and the second frequency group 720 includes frequencies above 5.0 kHz. In an example, the first frequency group 710 includes frequencies below 0.1 kHz and the second frequency group 720 includes frequencies above 8.0 kHz. In an example, the first frequency group 710 includes frequencies below 0.1 kHz and the second frequency group 720 includes frequencies above 11 kHz. In an example, the first frequency group 710 includes frequencies below 0.1 kHz and the second frequency group 720 includes frequencies above 14 kHz. In an example, the first frequency group 710 includes frequencies below 0.1 kHz and the second frequency group 720 includes frequencies above 17 kHz. In an example, the first frequency group 710 includes frequencies below 0.3 kHz and the second frequency group 720 includes frequencies above 5.0 kHz. In an example, the first frequency group 710 includes frequencies below 0.3 kHz and the second frequency group 720 includes frequencies above 8.0 kHz. In an example, the first frequency group 710 includes frequencies below 0.3 kHz and the second frequency group 720 includes frequencies above 11 kHz. In an example, the first frequency group 710 includes frequencies below 0.3 kHz and the second frequency group 720 includes frequencies above 14 kHz. In an example, the first frequency group 710 includes frequencies below 0.3 kHz and the second frequency group 720 includes frequencies above 17 kHz. In an example, the first frequency group 710 includes frequencies below 0.6 kHz and the second frequency group 720 includes frequencies above 5.0 kHz. In an example, the first frequency group 710 includes frequencies below 0.6 kHz and the second frequency group 720 includes frequencies above 8.0 kHz. In an example, the first frequency group 710 includes frequencies below 0.6 kHz and the second frequency group 720 includes frequencies above 11 kHz. In an example, the first frequency group 710 includes frequencies below 0.6 kHz and the second frequency group 720 includes frequencies above 14 kHz. In an example, the first frequency group 710 includes frequencies below 0.6 kHz and the second frequency group 720 includes frequencies above 17 kHz. In an example, the first frequency group 710 includes frequencies below 1.0 kHz and the second frequency group 720 includes frequencies above 5.0 kHz. In an example, the first frequency group 710 includes frequencies below 1.0 kHz and the second frequency group 720 includes frequencies above 8.0 kHz. In an example, the first frequency group 710 includes frequencies below 1.0 kHz and the second frequency group 720 includes frequencies above 11 kHz. In an example, the first frequency group 710 includes frequencies below 1.0 kHz and the second frequency group 720 includes frequencies above 14 kHz. In an example, the first frequency group 710 includes frequencies below 1.0 kHz and the second frequency group 720 includes frequencies above 17 kHz. In an example, the first frequency group 710 includes frequencies below 1.5 kHz and the second frequency group 720 includes frequencies above 5.0 kHz. In an example, the first frequency group 710 includes frequencies below 1.5 kHz and the second frequency group 720 includes frequencies above 8.0 kHz. In an example, the first frequency group 710 includes frequencies below 1.5 kHz and the second frequency group 720 includes frequencies above 11 kHz. In an example, the first frequency group 710 includes frequencies below 1.5 kHz and the second frequency group 720 includes frequencies above 14 kHz. In an example, the first frequency group 710 includes frequencies below 1.5 kHz and the second frequency group 720 includes frequencies above 17 kHz.

Figure 8:
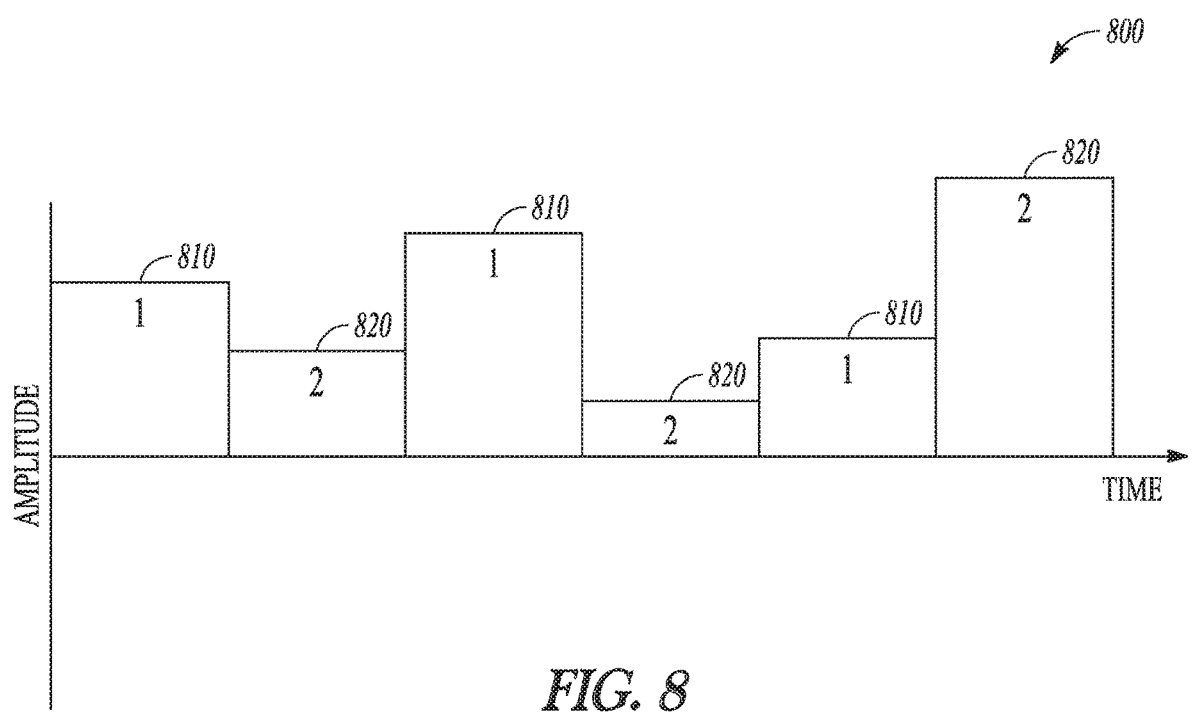
FIG. 8 illustrates an example of a composite waveform for providing a paresthesia therapy.

FIG. 8 illustrates an example of a composite waveform 800 for providing a supra-perception therapy such as a therapy that induces paresthesia. In an example, composite waveform 800 includes a first group of one or more frequencies 810 and second group of one or more frequencies 820. The first group of one or more frequencies and the second group of one or more frequencies may include frequencies in the range of 0.001 kHz to 20 kHz. In an example, the first group of one or more frequencies 810 may include frequencies below 2.0 kHz and the second group of one or more frequencies 820 may include frequencies above 2.0 kHz. In an example, the first group of one or more frequencies 810 may have an average frequency in the range of 0.001 kHz to 2.0 kHz and the second group of one or more frequencies 820 may have an average frequency in the range of 2.0 kHz to 20 kHz. In an example, the amplitude of the first group of one or more frequencies 810 can vary with time and the second group of one or more frequencies 820 can vary with time. In an example, composite waveform 800 may provide a supra-perception therapy.

Figure 9:
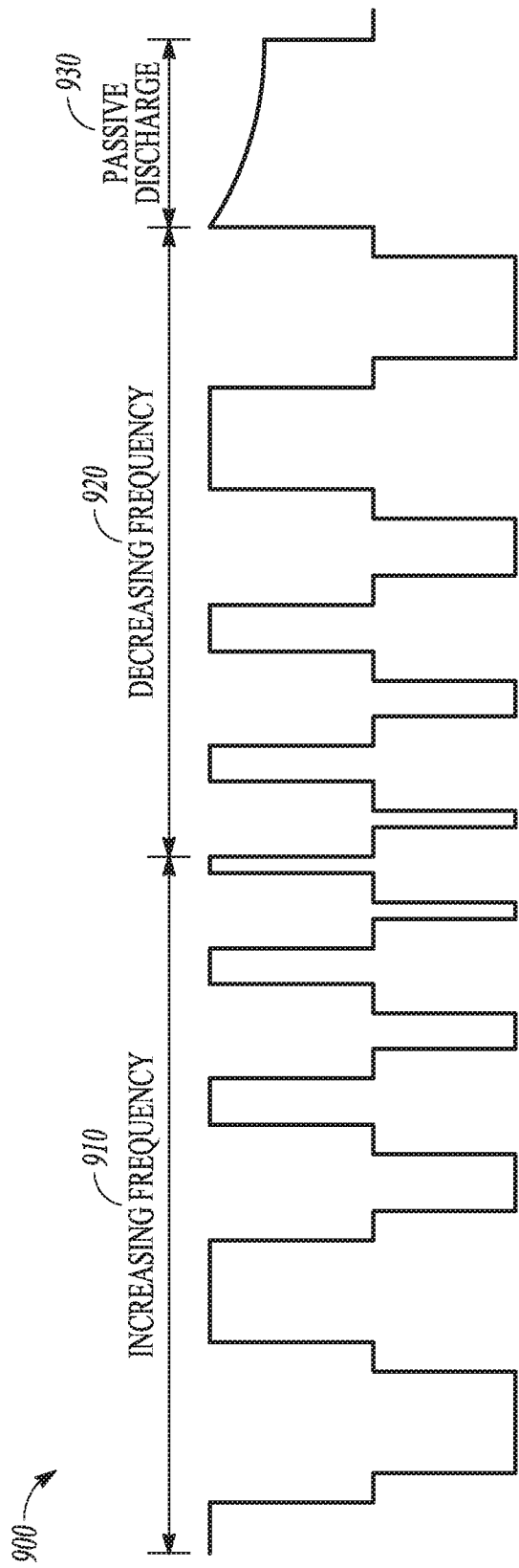
FIG. 9 illustrates an example of a frequency modulated waveform for providing a paresthesia therapy.

FIG. 9 illustrates an example of a frequency modulated waveform for providing a supra-perception therapy such as a therapy that induces paresthesia. In an example, the frequency modulated waveform 900 includes a first waveform building block 910 where the frequency may continuously increase, and a second waveform building block 920 where the frequency may continuously decrease. In an example, the frequency modulated waveform 900 includes a first waveform building block 910 where the frequency may continuously decrease, and a second waveform building block 920 where the frequency may continuously increase. In some examples, the frequency modulated waveform may include a third waveform building block 930 that includes a passive or active discharge. In an example, the waveform building blocks may be arranged in any order to form a sequence for providing a a-perception therapy.

Figure 10A:
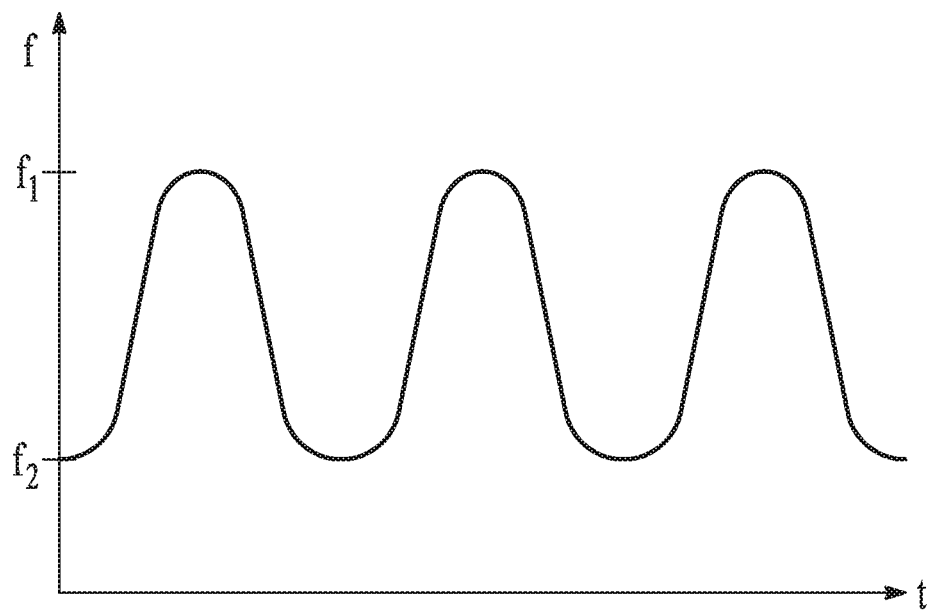
FIGS. 10A and 10B illustrate examples of frequency modulation for providing a paresthesia therapy.
Figure 10B:
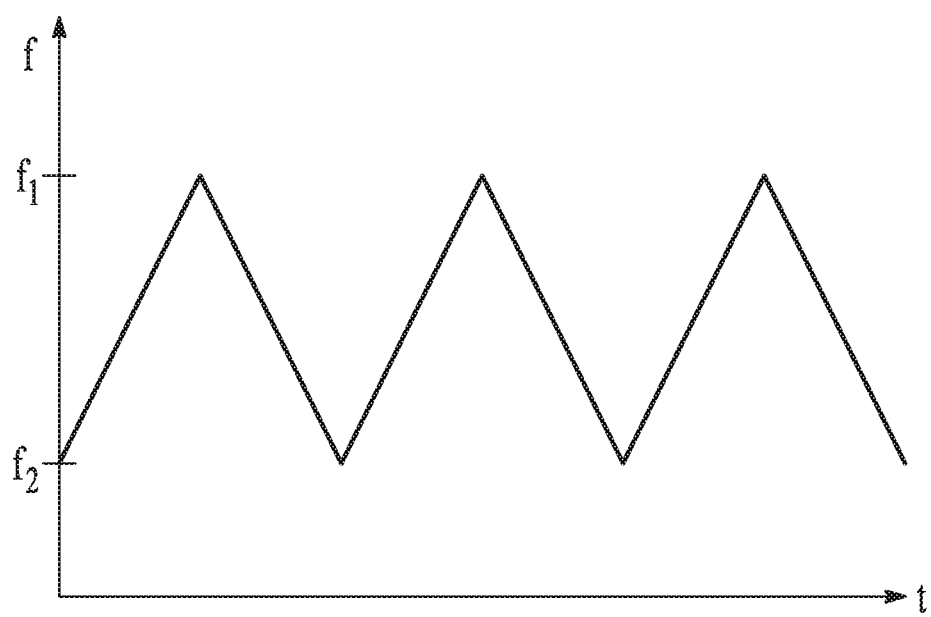

FIG. 10A illustrates an example of a frequency modulated waveform for providing a supra-perception therapy such as a therapy that induces paresthesia. In an example, the frequency modulated waveform may have a sinusoidal shape and vary between an upper frequency $f_2$ and a lower frequency $f_1$. FIG. 10B illustrates an example of frequency modulation for providing a supra-perception therapy such as a therapy that induces paresthesia. In an example, the frequency modulation waveform may have a triangular shape and vary between an upper frequency $f_2$ and a lower frequency $f_1$. Frequency modulation waveforms such as those illustrated in FIG. 10A and FIG. 10B may include different waveform shapes. The waveform shapes may include regular shapes (e.g. square, sinusoidal, triangular, saw tooth, and the like) or irregular shapes. The waveform shapes may include regular or irregular patterns.

FIG. 11 illustrates an example of a composite waveform for providing a supra-perception therapy such as a therapy that induces paresthesia. In an example, composite waveform 1100 includes a first waveform building block 1110, a second waveform building block 1120, a third waveform building block 1130, and a fourth waveform building block 1140. The first waveform building block may include frequencies below 1.2 kHz. The second waveform building block may include an anodic or cathodic recharge such as may be useful to provide charge balancing. Rather than having separate first and second building blocks, these waveforms, including the recharge, may be included in a single waveform building block. The third waveform may include frequencies above 1.5 kHz. The fourth waveform building block may include frequencies below 1.2 kHz. In an example, the waveform building blocks may be arranged in any order to form a sequence for providing a supra-perception therapy.

Figure 12:
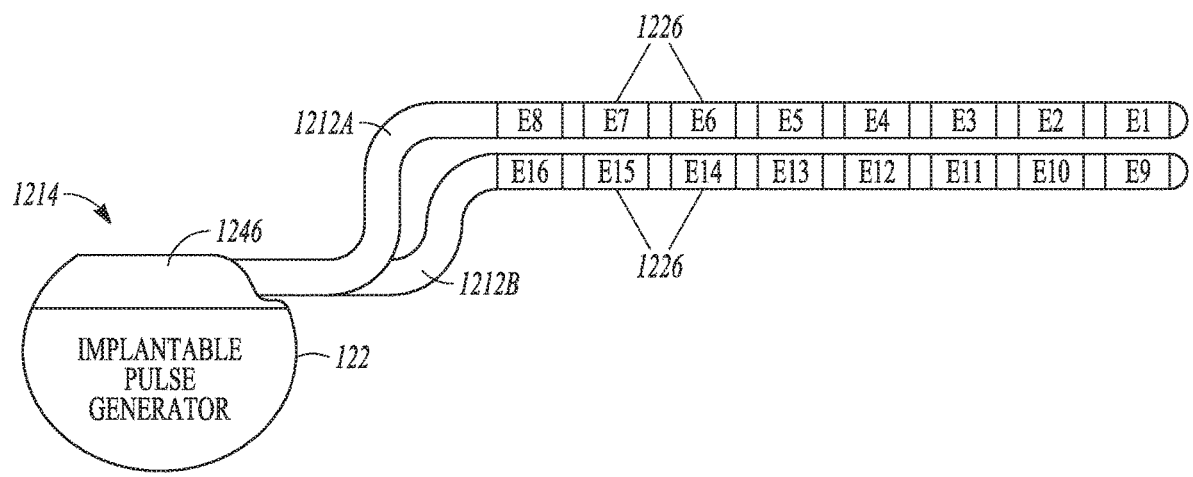
FIG. 12 illustrates an example of an implantable pulse generator (IPG) and percutaneous leads.

FIG. 12 illustrates an example of a profile view of an implantable pulse generator (IPG) 1244 and percutaneous leads 1212. One of the neuromodulation leads 12a may have eight electrodes 26 (labeled E1-E8), and the other neuromodulation lead 12b may have eight electrodes 26 (labeled E9-E16). The actual number and shape of leads and electrodes may, of course, vary according to the intended application. The IPG 14 may comprise an outer case 44 for housing the electronic and other components (described in further detail below), and a connector 46 to which the proximal ends of the neuromodulation leads 12 mates in a manner that electrically couples the electrodes 26 to the electronics within the outer case 44. The outer case 44 may be composed of an electrically conductive, biocompatible material, such as titanium, and forms a hermetically sealed compartment wherein the internal electronics are protected from the body tissue and fluids. In some examples, the outer case 44 may serve as an electrode.

In an example, the IPG 14 includes a battery and pulse generation circuitry that delivers the electrical modulation energy in the form of one or more electrical pulse trains to the electrode array 26 in accordance with a set of modulation parameters programmed into the IPG 14. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the modulation on duration X and modulation off duration Y).

In an example, electrical modulation may occur between two (or more) activated electrodes, one of which may be the IPG case 44. Modulation energy may be transmitted to the tissue in a monopolar or multipolar (e.g., bipolar, tripolar, etc.) fashion. Monopolar modulation may occur when a selected one of the lead electrodes 26 is activated along with the case of the IPG 14, so that modulation energy is transmitted between the selected electrode 26 and case. Bipolar modulation may occur when two of the lead electrodes 26 are activated as anode and cathode, so that modulation energy is transmitted between the selected electrodes 26. For example, electrode E3 on the first lead 12a may be activated as an anode at the same time that electrode E11 on the second lead 12a is activated as a cathode. Tripolar modulation may occur when three of the lead electrodes 26 are activated, two as anodes and the remaining one as a cathode, or two as cathodes and the remaining one as an anode. For example, electrodes E4 and E5 on the first lead 12a may be activated as anodes at the same time that electrode E12 on the second lead 12b is activated as a cathode. The modulation energy may be delivered between a specified group of electrodes as monophasic electrical energy or multiphasic electrical energy.

Figure 13:
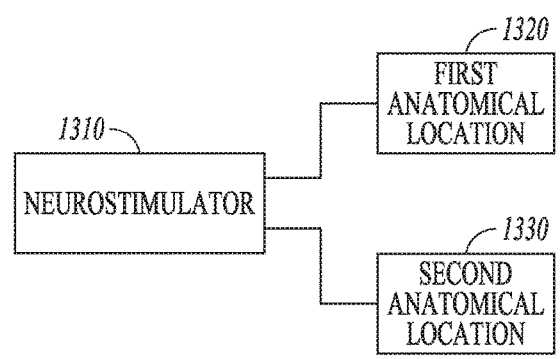
FIG. 13 illustrates an example of a neurostimulator configured to provide a paresthesia therapy.

FIG. 13 illustrates an example of a neurostimulator configured to provide a sub-perception therapy. In an example, the neurostimulator 1310 may provide neurostimulation energy, such as in the form of a first electrical waveform to a first anatomical location 1320 to generate an electrical field and deliver a sub-perception therapy. In an example, the first electrical waveform may have a frequency of less than 2.0 kHz, and may be targeted to modulate the dorsal horn, dorsal root, dorsal column, or dorsal root ganglia. In an example, the first anatomical location may include a T7 and T8 vertebrae. The neurostimulator 1310 may also provide neurostimulation energy, such as in the form of a second electrical waveform to a second anatomical location 1330 to generate an electrical field and deliver a sub-perception therapy. In an example, the second electrical waveform may have a frequency of less than 2.0 kHz, and may be targeted to modulate the dorsal horn, dorsal root, dorsal column, or dorsal root ganglia. In an example, the second anatomical location may include a T8, T9, and T10 vertebrae.

The above detailed description is intended to be illustrative, and not restrictive. The scope of the disclosure should, therefore, be determined with references to the appended claims, along with the full scope of equivalents to which such claims are entitled.

What is claimed is:

1. A method, comprising:
  applying a single pain therapy to a patient using an implantable neuromodulation system, wherein providing the single pain therapy includes:
  delivering to the patient an electrical waveform, wherein the electrical waveform includes pulses and bursts of pulses and the electrical waveform has different pulse-to-pulse intervals such that the electrical waveform has a distribution of frequencies in the range of 0.001 kHz to 20 kHz, wherein the distribution of frequencies for the electrical waveform includes at least two frequencies caused by different pulse-to-pulse intervals less than a threshold frequency value and at least two frequencies caused by different pulse-to-pulse intervals above the threshold frequency value, wherein the threshold frequency value is 0.3 kHz.

2. The method of claim 1, wherein the delivering to the patient the electrical waveform includes delivering the electrical waveform to modulate a dorsal column.

3. The method of claim 1, wherein the single pain therapy is a supra-perception therapy.

4. The method of claim 1, wherein the electrical waveform includes a composite waveform.

5. The method of claim 1, wherein the delivering to the patient the electrical waveform includes delivering the electrical waveform to one neural target.

6. The method of claim 1, wherein the delivering to the patient the electrical waveform includes delivering the electrical waveform to more than one neural target.

7. The method of claim 1, wherein the electrical waveform includes a regular pattern of waveform shapes.

8. The method of claim 1, wherein electrical the waveform incudes an irregular pattern of waveform shapes.

9. The method of claim 1, wherein the pulses and the bursts of pulses in the electrical waveform are arranged in a predefined sequence of bursts of pulses with respect to pulses.

10. The method of claim 1, wherein the at least two frequencies above the threshold frequency threshold include one or more frequencies above 8.0 kHz.

11. The method of claim 1, wherein the at least two frequencies above the threshold frequency threshold include one or more frequencies above 2 kHz.

12. The method of claim 1, wherein the at least two frequencies less than the threshold frequency value include one or more frequencies below 0.1 kHz.

13. The method of claim 1, wherein the electrical waveform includes concatenated temporal waveform segments.

14. The method of claim 13, wherein the concatenated temporal waveform segments include at least one segment with at least one pulse and at least one segment with a burst of pulses.

15. A method implemented using a graphical user interface, comprising:
receiving, via the graphical user interface, at least one user input to determine an electrical waveform to be delivered to the patient for a single pain therapy, wherein the electrical waveform includes pulses and bursts of pulses having different pulse-to-pulse intervals such that the electrical waveform has a distribution of frequencies in the range of 0.001 kHz to 20 kHz, wherein the distribution of frequencies for the electrical waveform includes at least two frequencies caused by different pulse-to-pulse intervals less than a threshold frequency value and at least two frequencies caused by different pulse-to-pulse intervals above the threshold frequency value, wherein the threshold frequency value is 0.3 kHz.

16. The method of claim 15, wherein the electrical waveform includes concatenated temporal waveform segments, the concatenated temporal waveform segments including more than one regular pattern of waveform shapes.

17. A neuromodulation system comprising:
a first storage device configured to store a waveform pattern including pulses and bursts of pulses having different pulse-to-pulse intervals; and
modulation circuitry configured to provide at least a single pain therapy by delivering an electrical waveform to a patient, the electrical waveform for the single pain therapy including the stored waveform pattern having the different pulse-to-pulse intervals such that the electrical waveform has a distribution of frequencies in the range of 0.001 kHz to 20 kHz, wherein the distribution of frequencies for the electrical waveform includes at least two frequencies caused by different pulse-to-pulse intervals less than a threshold frequency value and at least two frequencies caused by different pulse-to-pulse intervals above the threshold frequency value, wherein the threshold frequency value is 0.3 kHz.

18. The neuromodulation system of claim 17, wherein the electrical waveform includes concatenated temporal waveform segments, and the concatenated temporal waveform segments include segments with at least one pulse and segments with a burst of pulses.

19. The neuromodulation system of claim 17, wherein the electrical waveform includes a regular pattern of waveform shapes.

20. The neuromodulation system of claim 17, wherein the pulses and the bursts of pulses in the electrical waveform are arranged in a predefined sequence of bursts of pulses with respect to pulses.

* * * * *